(12) United States Patent
Alig et al.

(10) Patent No.: US 6,297,266 B1
(45) Date of Patent: Oct. 2, 2001

(54) THIAZOLE DERIVATIVES

(75) Inventors: Leo Alig, Kaiseraugst; Kurt Hilpert, Hofstetten; Thomas Weller, Basle, all of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/420,387

(22) Filed: Oct. 19, 1999

(30) Foreign Application Priority Data

Oct. 22, 1998 (EP) .................................................. 98119985

(51) Int. Cl.$^7$ ........................ C07D 277/48; A01K 31/427
(52) U.S. Cl. ........................ 514/370; 514/371; 548/194; 548/196
(58) Field of Search .................................. 548/196, 194; 514/370, 371

(56) References Cited

U.S. PATENT DOCUMENTS 5,430,024   7/1995   Alig et al. .

FOREIGN PATENT DOCUMENTS

| 417 751 | 3/1991 | (EP) . |
| 445 796 | 9/1991 | (EP) . |
| 928 790 | 7/1999 | (EP) . |
| 928 793 | 7/1999 | (EP) . |
| WO 96 22966 | 8/1996 | (WO) . |

OTHER PUBLICATIONS

Schur, R.C., et al., J. Med. Chem., 34, p 914 (1991).
Plazzi, P.V., et al., Il Farmaco, 44, (11), pp 1011–1030 (1989).
Barton, A., et al., J. Chem. Soc. Perkin I, pp 159–164 (1982).
Org. Syn. Coll. IV, pp 573–576.
Abdallah–El Ayoubi, S., et al., Synthesis, pp 258–260 (1994).
Fischer, R.H., et al., Synthesis, pp53–54 (1976).
Kaminsky, Z.J., Synthesis, pp 917–920 (1987).
Verardo, G., et al., Synthesis pp 121–125 (1993).
Wolfe, J.P., et al., Tetrahedron letters, 38, pp 6367–6370 (1997).
Buchwald S.L., et al., Tetrahedron Letters, 38, pp 6359–6362 (1997).
Buchwald S.L., et al., J. Org. Chem., 62, pp 6066–6068 (1997).
Ma, D., et al., Tetrahedron: Asymmetry, 9, pp 1137–1142 (1998).
Christensen, l., et al., Nucleic Acids Res., 26, pp 2735–2739 (1998).
Weitz, I.S., et al., J. Org. Chem., 62, pp 2527–2534 (1997).
Hermkens, et al., Tetrahedron, 44, pp 1991–2000 (1988).
Kihlberg, J., et al., Acta Chem. Scand., B37, pp 911–916 (1983).
Katopodis, A.G., et al., Biochemistry, 29, pp 4541–4548 (1990).
Davies, S.G., et al., J. Chem. Soc. Perkin Trans. I, pp 2597–2604.
Leanna, M.R., et al., Tetrahedron Letters, 33, pp 5029–5032.
Poss, M.A., et al., Tetrahedron Letters, 33, pp 5933–5936 (1992).
Kim, K., Tetrahedron Letters, 29, pp 3183–3186 (1988).
Alig, L., J. Med. Chem., 35, pp 4393–4407 (1992).
Chemical Abstracts, v. 127, abstract No. 17675n, Jul. 14, 1997.

*Primary Examiner*—Robert Gerstl
(74) *Attorney, Agent, or Firm*—George W. Johnston; William H. Epstein; John P. Parise

(57) ABSTRACT

Compounds of formula (I)

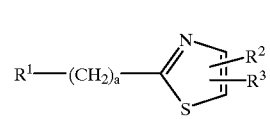

as well as pharmaceutically usable salts and esters thereof, wherein $R^1$, $R^2$ and $R^3$ have the significance described in the specification, inhibit the binding of adhesive proteins to the surface of different types of cell and accordingly influence cell-cell and cell-matrix interactions. They can be used in the form of pharmaceutical preparations in the control or prevention of neoplasms, tumor metastasizing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi.

57 Claims, No Drawings

THIAZOLE DERIVATIVES

BACKGROUND OF THE INVENTION

The present invention is concerned with novel thizzole derivatives. The derivatives inhibit the binding of adhesive proteins to the surface of different types of cell by influencing cell-cell and cell-matrix interactions.

SUMMARY OF THE INVENTION

The subject invention provides compounds of formula:

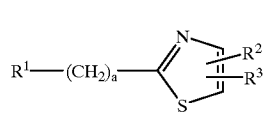
(I)

wherein $R^1$ is

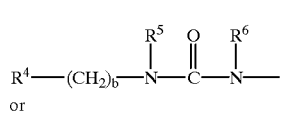

or

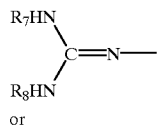

or

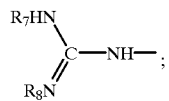

$R^2$ is

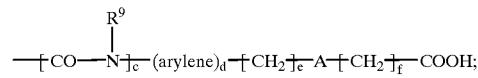
(II)

$R^3$ is hydrogen, alkyl, cycloalkyl, aryl, aralkyl, heteroaryl, carboxy, alkyl-O—CO— or aralkyl-O—CO—;
$R^4$ is hydrogen, alkyl, cycloalkyl, aryl or heteroaryl;
$R^5$ and $R^6$, independent of one another, are hydrogen, alkyl, cycloalkyl or heteroaryl;
$R^7$ and $R^8$, independent of one another, are hydrogen, alkyl, cycloalkyl or heteroaryl or $R^7$ and $R^8$, together with the N atoms to which they are attached form a 5- to 8-membered heterocyclic ring which can carry one or more alkyl substituents;
$R^9$ is hydrogen, alkyl or cycloalkyl;
$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, aryl-sulphonyl or heteroarylsulphonyl;

A is oxygen, sulphur, —CH═CH— or 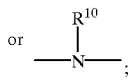;

a to f are zero or whole positive integers, with a being zero to 2; b being zero to 4; c and d being zero or 1, with the proviso that c and d are not both simultaneously zero; e is zero to 5, with the proviso that e is other than zero when d is zero and e is zero to 3 when A is equal to —CH═CH—; and f is zero to 3, with the proviso that f is not zero when A is oxygen, sulphur or

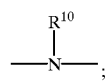;

and their pharmaceutically usable salts and esters.

A preferred group of compounds are those of the formula:

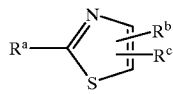

wherein, $R^a$ is

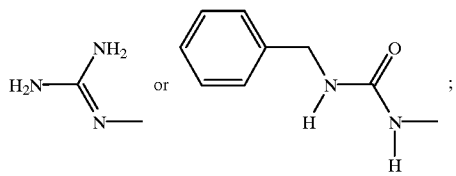

$R^b$ is

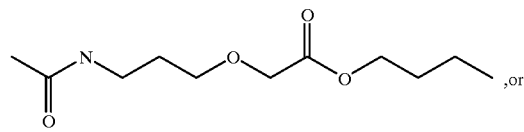

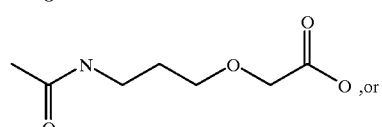

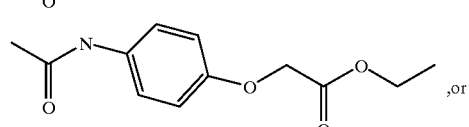

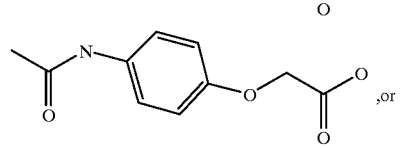

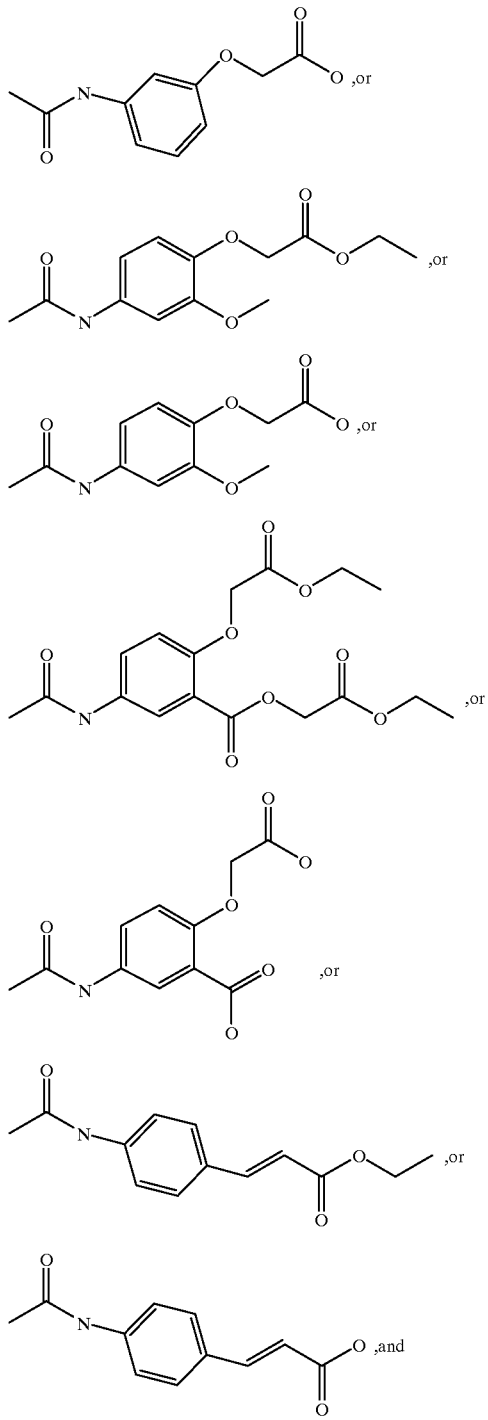

$R^c$ is hydrogen or methyl.

A first series of preferred compounds have $R^a$ being

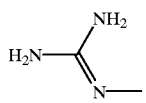

and $R^b$ being

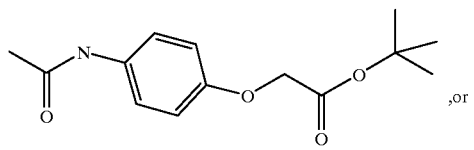

When $R^c$ is methyl, the more preferred compounds of this first series are butyl {3-[(2-guanidino-4-methyl-thiazole-5-carbonyl)-amino]-propoxy}-acetate, [3-[(2-guanidino-4-methyl-thiazole-5-carbonyl)-amino]-propoxy]-acetic acid hydrochloride, ethyl {4-[(2-guanidino-4-methyl-thiazole-5-carbonyl)-amino]-phenoxy}-acetate, [4-[(2-guanidino-4-methyl-thiazole-5-carbonyl)-amino]-phenoxy]-acetic acid hydrochloride, tert-butyl {3-[(2-guanidino-4-methyl-thiazole-5-carbonyl)-amino]-phenoxy}-acetate, and [3-[(2-guanidino-4-methyl-thiazole-5-carbonyl)-amino]-phenoxy]-acetic acid.

When $R^c$ is hydrogen, the more preferred compounds of this first series are ethyl {4-[(2-guanidino-thiazole-4-carbonyl)-amino]-phenoxy}-acetate, [4-[(2-guanidino-thiazole-4-carbonyl)-amino]-phenoxy]-acetic acid hydrochloride, ethyl {4-[(2-guanidino-thiazole-5-carbonyl)-amino[-phenoxy}-acetate, and [4-[(2-guanidino-thiazole-5-carbonyl)-amino]-phenoxy]-acetic acid hydrochloride.

A second series of preferred compounds have $R^a$ being

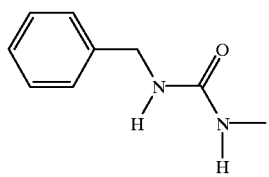

$R^c$ being hydrogen, and $R^b$ being

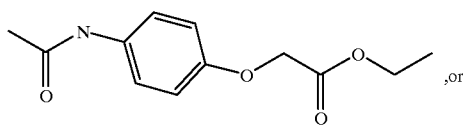, or

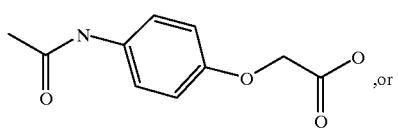, or

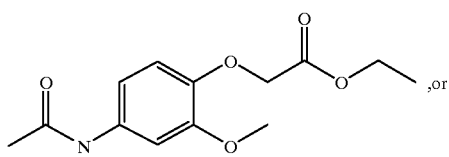, or

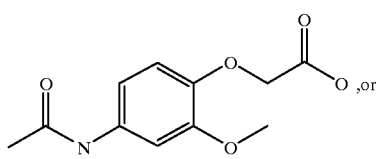, or

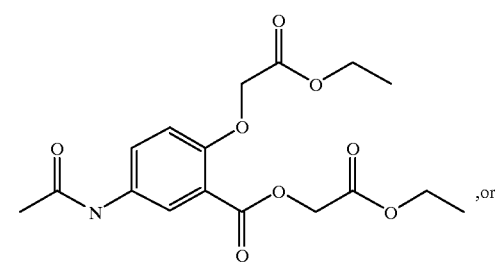, or

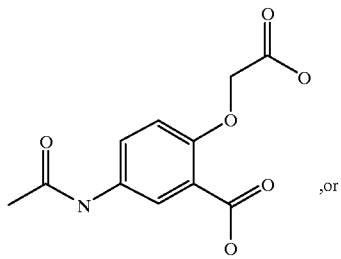, or

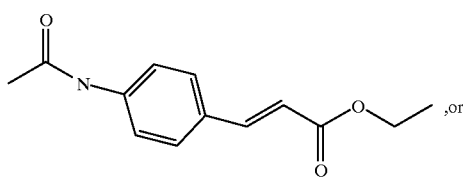, or

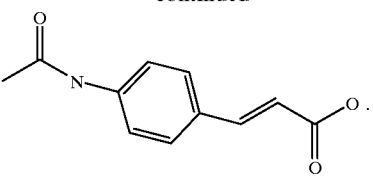

In this second series, the preferred compounds are ethyl (4-{[2-(3-benzyl-ureido)-thiazole-4-carbonyl]-amino}-phenoxy)-acetate, [4-[[2-(3-benzyl-ureido)-thiazole-4-carbonyl]-amino]-phenoxy]-acetic acid, ethyl (4-{[2-(3-benzyl-ureido)-thiazole-4-carbonyl]-amino}-2-methoxy-phenoxy)-acetate, (4-{[2-(3-benzyl-ureido)-thiazole-4-carbonyl]-amino}-2-methoxy-phenoxy)-acetic acid, ethoxycarbonylmethyl 5-{[2-(3-benzyl-ureido)-thiazole-4-carbonyl]-amino}-2-ethoxycarbonylmethoxy-benzoate, 5-{[2-(3-benzyl-ureido)-thiazole-4-carbonyl]-amino}-2-carboxymethoxy-benzoic acid, ethyl (E)-3-[4-[[2-(3-benzyl-ureido)-thiazole-4-carbonyl]-amino]-phenyl]-acrylate, and (E)-3-[4-[2-(3-benzyl-ureido)-thiazole-4-carbonyl]-amino]-phenyl]-acrylic acid.

DETAILED DESCRIPTION OF THE INVENTION

The subject invention will now be described in terms of its preferred embodiments. These embodiments are set forth to aid in understanding the invention but are not to be construed as limiting.

The present invention is concerned especially with thiazole derivatives of formula (I)

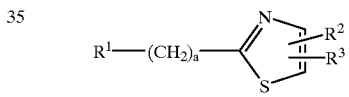

wherein
$R^1$ is

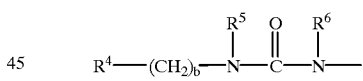
or

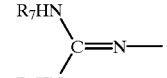
or

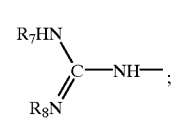

$R^2$ is

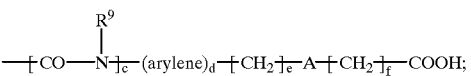

R³ is hydrogen, alkyl, cycloalkyl, aryl, aralkyl, heteroaryl, carboxy, alkyl-O—CO— or aralkyl-O—CO—;
R⁴ is hydrogen, alkyl, cycloalkyl, aryl or heteroaryl;
R⁵ and R⁶ independently of one another are hydrogen, alkyl, cycloalkyl or heteroaryl;
R⁷ and R⁸ independently of one another are hydrogen, alkyl, cycloalkyl or heteroaryl or R⁷ and R⁸ together with the N atoms to which they are attached form a 5- to 8-membered heterocyclic ring which can carry one or more alkyl substituents;
R⁹ is hydrogen, alkyl or cycloalkyl;
R¹⁰ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, aryl-sulphonyl or heteroarylsulphonyl;
A is oxygen, sulphur, —CH=CH— or 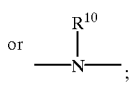

a to f are zero or whole positive integers, with a being zero to 2; b being zero to 4; c and d being zero or 1, with the proviso that c and d are not both simultaneously zero; e is zero to 5, with the proviso that e is other than zero when d is zero and e is zero to 3 when A is equal to —CH=CH—; and f is zero to 3, with the proviso that f is not zero when A is oxygen, sulphur or

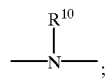

and their pharmaceutically usable salts and esters.

Further objects of the invention are the compounds of formula (I) described above for use as therapeutically active substances.

The compounds of formula (I) described above can be used for the production of medicaments for the prophylaxis and therapy of illnesses which are based on a malfunction of the binding of adhesive proteins to vitronectin receptors.

The subject invention provides pharmaceutical compositions containing a compound of formula (I) described above and a therapeutically inert carrier, such pharmaceutical compositions may additionally contain one or more compounds of formula (I) or additionally one or more compounds selected from the group comprising anticoagulants, fibrinolytics as well as medicaments for the prophylaxis and therapy of illnesses which are based on a malfunction of the binding of adhesive proteins to vitronectin receptors.

An object of the invention is to use the compounds of formula (I) described above for the production of medicaments for the treatment or prophylaxis of illnesses which are based on a malfunction of the binding of adhesive proteins to vitronectin receptors. Such medicaments may be used for the treatment or prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi. Treatment and prophylasis of such illnesses typically comprise the administration of an effective amount of a compound of formula (I).

In the present description the term "alkyl", alone or in combination, signifies a straight-chain or branched-chain alkyl group with 1 to 8 carbon atoms, preferably a straight-chain or branched-chain alkyl group with 1–4 carbon atoms. Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, isopropyl and tert-butyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopentyl and particularly cyclopentyl.

The term "alkoxy", alone or in combination, signifies an alkyl ether group in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

The term "aryl", alone or in combination, signifies a phenyl or naphthyl group which optionally carries one or more substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert-butoxyphenyl, 4-fluorophenyl, 2-chlorophenyl, 3-chlorophenyl, 4-chlorophenyl, 4-hydroxyphenyl, 1-naphtlyl, 2-naphthyl. Alkoxy-phenyls and chlorophenyls are preferred, especially phenyl and ortho-, meta- and para-monochlorophenyls, specially para- and meta-chlorophenyl and para- and meta-methoxyphenyl. Phenyl is particularly preferred.

The term "aryloxy", alone or in combination, signifies a group of the formula -O-aryl in which the term "aryl" has the previously given significance.

The term "aralkyl", alone or in combination, signifies an alkyl or cycloalkyl group as previously defined in which one hydrogen atom is replaced by an aryl group as previously defined, such as, for example, benzyl, 2-phenylethyl and the like, preferably benzyl.

The term "aralkoxy", alone or in combination, signifies an aralkyl group as previously defined in which one hydrogen atom of the alkyl part is replaced by an oxygen atom which carried the free valency. Benzyloxy is preferred.

The term "arylene", alone or in combination, signifies a phenylene or a naphthylene group which optionally carries one or more substituents selected from alkyl, cycloalkyl, halogen, hydroxy, amino, nitro, aryloxy, aralkoxy, alkoxy-alkoxy and preferably alkoxy, carboxy and —CO—O—$CH_2$—CO—O-alkyl. Examples are ortho-, meta- or para-phenylene, the tolylenes, the methoxyphenylenes, the tert. butoxyphenylenes, the fluorophenylenes, the chlorophenylenes, the hydroxyphenylenes, the naphthylenes the benzyloxyphenylenes etc. Preferred are meta- and para-phenylenes, with the substituents of the phenylene previously given by the definition of R² standing meta or para to one another and whereby in addition one or more substituents selected from alkyl, cycloalkyl, halogen, hydroxy, amino, aryloxy and alkoxy-alkoxy and preferably alkoxy, carboxy and —CO—O—$CH_2$—CO—O-alkyl can be present on the arylene ring. Especially preferred are meta- and para-phenylene which carry one of the previously named substituents on the phenylene ring and in this case there are most particularly preferred the meta- and para-phenylenes which carry methoxy, carboxy or —CO—O—$CH_2$—CO—O-ethyl on the phenylene ring. Meta- and para-phenylene are particularly preferred.

The term "heterocyclyl", alone or in combination, signifies a saturated, partially unsaturated or aromatic 5 to 10 membered heterocycle which contains one or more hetero atoms selected from nitrogen, oxygen and sulphur. If desired, it can be substituted on one or more carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, halogen, alkyl, cycloalkyl and alkoxy are preferred. Examples of such heterocyclyl groups are pyrrolidinyl, piperidinyl, piperazinyl, morpholinyl, thiomorpholinyl, pyrrolyl, imidazolyl (e.g. imidazol-4-yl, 1-benzyloxy-carbonylimidazol-4-yl), pyrazolyl, pyridyl, pyrazinyl, pyrimidinyl, hexahydropyrimidinyl, furyl, thienyl, thiazolyl, oxazolyl, thiazolyl, indolyl (e.g. 2-indolyl), quinolyl (e.g. 2-quinolyl, 3-quinolyl, 1-oxido-2-quinolyl), isoquinolyl (e.g. 1-isoquinolyl, 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred are 5- or 6-membered rings, especially piperidyl and pyridyl.

The term "heteroaryl", alone or in combination, signifies the aromatic compounds which fall under the definition of "heterocyclyl" and which can carry the substituents described there. Preferred are 5- and 6-membered rings, especially pyridyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyletylamino, pyrrolidin-1-yl or piperidino etc., preferably amino, dimethylamino and diethylamino, particularly primary amino.

The term "halogen" signifies fluorine, chlorine, bromine or iodine, preferably chlorine.

The term "alkyl-O—CO—" signifies an alkyl ester group in which alkyl is as previously defined. In this case the methyl ester, ethyl ester, the isomreric propyl ester and the isomeric butyl ester groups are preferred. The methyl ester and ethyl ester groups are especially preferred.

The term "aralkyl-O—CO—" signifies an aralkyl ester group in which aralkyl is as previously defined. In this case the benzyl ester group is preferred.

The term "heterocyclylalkyl" signifies an alkyl group as previously defined in which a hydrogen atom has been replaced by a heterocyclyl group. Pyridylmethyl, 1-pyridylethyl and 2-pyridylethyl are examples of such heterocyclylalkyls.

The term "alkylsulphonyl" signifies a

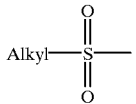

group in which alkyl is as previously defined. Preferred "alkylsulphonyls" are methylsulphonyl, ethylsulphonyl, the isomeric propylsulphonyls and the isomeric butylsulphonyls.

The term "arylsulphonyl" signifies a

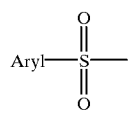

group in which aryl is as previously defined. Preferred arylsulphonyls are phenylsulphonyl, 1-naphthylsulphonyl, 2-naphthylsulphonyl and 2-mesitylenesulphonyl.

The term "heteroarylsulphonyl" signifies a

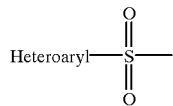

group in which heteroaryl is as previously defined. Preferred heteroarylsulphonyls are 2-thiophenesulphonyl and 3,5-dimethylisoxazole-4-sulphonyl.

The term "alkyl-CO—" signifies an alkylcarbonyl group in which alkyl is as previously defined. Methyl- and ethyl-carbonyl are preferred example's.

Examples of physiologically usable salts of the compounds of formula I are salts with physiologically compatible mineral acids such as sulphuric acid, phosphoric acid or preferably hydrochloric acid; or with organic acids such as methanesulphonic acid, acetic acid, trifluoroacetic acid, citric acid, fumaric acid, maleic acid, tartaric acid, succinic acid or salicylic acid. The compounds of formula I having a free carboxy group can also form salts with physiologically compatible bases. Examples of such salts are alkali metal, alkaline earth metal, ammonium and alkylammonium salts such as the Na, K, Ca or tetramethylammonium salt. The compounds of formula I can also exist in the form of zwitterions.

In the nomenclature used in the present description the ring atoms of the thiazole ring are numbered as follows:

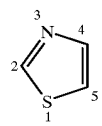

with substituent $R^1$ being bonded to position 2 and the substituents $R^2$ being bonded to position 4 and $R^3$ being bonded to position 5:

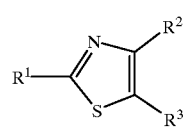

or $R^2$ being bonded to position 5 and $R^3$ being bonded to position 4 of the thiazole ring:

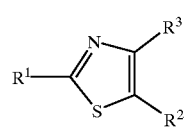

The invention expressly includes pharmaceutically suitable derivatives of the compounds of formula I. For example, the COOH groups in $R^2$ can be esterified. Examples of suitable esters are the alkyl and aralkyl esters. Preferred esters are the methyl, ethyl, propyl, butyl, benzyl and (R/S)-1-((isopropoxy-carbonyl)-oxy)-ethyl ester. The ethyl esters and the isomeric butyl esters are especially preferred.

The compounds of formula I can also be solvated, e.g. hydrated. The hydration can be effected in the course of the manufacturing process or can take place e.g. as a consequence of hygroscopic properties of an initially anhydrous compound of formula I (hydration).

The compounds of formula I can contain several asymmetric centres and can exist in the form of optically pure enantiomers, mixtures of enantiomers such as, for example, racemates, optically pure diastercoisomers, mixtures of diastereoisomers, diastereoisomeric racemates or mixtures of diastereoisomeric racemates.

Examples of preferred compounds of formula (I) are those in which $R^2$ is

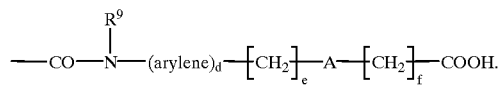
(III)

Also preferred are the above compounds of formula (I) in which $R^2$ is

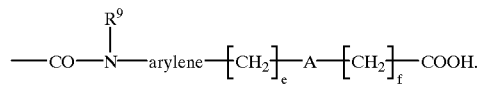
(IV)

Likewise preferred compounds of formula (I) are those in which $R^2$ is

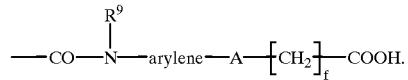
(V)

To the preferred compounds there furthermore belong those in which $R^2$ is

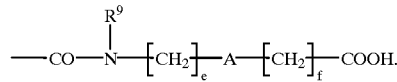
(VI)

Compounds of formula (I) in which A is oxygen or —CH=CH— are preferred. Oxygen is especially preferred.

To the preferred compounds described above there furthermore belong those in which $R^1$ is

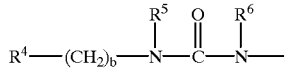

Furthermore, preferred compounds of formula (I) are those in which arylene is phenylene or substituted phenylene, with the substituted phenylene carrying one or more, preferably one, aralkoxy, halogen, alkoxy-alkoxy and especially alkoxy, carboxy or —CO—O—CH$_2$—CO—O-alkyl substituent.

Especially preferred are the above compounds of formula (I) in which arylene is meta- or para-phenylene or substituted meta- or para-phenylene, with the substituents of the phenylene previously given by the definition of $R^2$ standing meta- or para- to one another and with the substituted phenylene carrying an additional substituent selected from the group of alkoxy, carboxy or —CO—O—CH$_2$—CO—O-alkyl and particularly from the group of methoxy, carboxy and —CO—O—CH$_2$—CO—O-ethyl on the ring. Quite particularly preferred are the above compounds of formula (I) in which arylene is unsubstituted phenylene and especially unsubstituted meta- or para-phenylene.

A group of preferred compounds of formula (I) comprises those in which $R^3$ is hydrogen, alkyl, cycloalkyl or phenyl. Of these, especially preferred compounds are those in which $R^3$ is hydrogen or alkyl.

A further group of preferred compounds of formula (I) comprises those in which $R^4$ is hydrogen, alkyl, cycloalkyl or phenyl and particularly preferred are those in which $R^4$ is hydrogen or phenyl.

Also preferred are the above compounds of formula (I) in which $R^5$, $R^6$, $R^7$ and $R^8$ are hydrogen or $R^5$ and $R^6$ are both hydrogen and $R^7$ and $R^8$ together with the N atoms to which they are attached form a 5- to 6-membered ring. Of these there are especially preferred those in which $R^5$, $R^6$, $R^7$ and $R^8$ are hydrogen.

A further group of preferred compounds of formula (I) comprises those in which $R^9$ is hydrogen or cycloalkyl. Those in which $R^9$ is hydrogen are particularly preferred.

The preferred compounds of formula (I) in which A is

are those in which $R^{10}$ is alkyl or cycloalkyl and especially those in which $R^{10}$ is hydrogen. Particularly preferred are these compounds in which $R^{10}$ is phenyl.

Preferred compounds are compounds of formula (I) in which $R^2$ is bonded to position 4 and $R^3$ is bonded to position 5 of the thiazole ring. Of these there are especially preferred those in which $R^2$ is bonded to position 4 and $R^3$ is bonded to position 5 of the thiazole ring and $R^1$ is

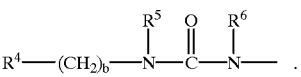

Likewise preferred are compounds of formula (I) in which a is equal to 1. Those in which a is zero are especially preferred.

Also preferred are compounds of formula (I) in which b is zero to 2 and especially those in which b is equal to 1.

Furthermore, compounds of formula (I) in which e is zero to 4 are preferred. Those in which e is equal to 3 and d is equal to zero are especially preferred.

Likewise especially preferred compounds in accordance with formula (I) are those in which e is equal to zero and d is equal to 1.

A further group of preferred compounds of formula (I) embraces those in which f is equal to 1 and A is equal to oxygen, sulphur or

and particularly in which A is oxygen. Likewise preferred are compounds of formula (I) in which f is equal to zero and A is —CH=CH—.

Furthermore, there are preferred compounds of formula (I) in which A is

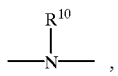

$R^{10}$ is phenyl, c is 1 and e is zero.

Examples of preferred compounds of formula I are:

Butyl {3-[(2-guanidino-4-methyl-thiazole-5-carbonyl)-amino]-propoxy}-acetate;

[3-[(2-guanidino-4-methyl-thiazole-5-carbonyl)-amino]-propoxy]-acetic acid hydrochloride;

ethyl {4-[(2-guanidino-4-methyl-thiazole-5-carbonyl)-amino]-phenoxy}-acetate;

[4-[(2-guanidino-4-methyl-thiazole-5-carbonyl)-amino]-phenoxy]-acetic acid hydrochloride;

butyl {3-[(2-guanidino-4-methyl-thiazole-5-carbonyl)-amino]-phenoxy}-acetate;

[3-[(2-guanidino-4-methyl-thiazole-5-carbonyl)-amino]-phenoxy]-acetic acid;

ethyl {4-[(2-guanidino-thiazole-4-carbonyl)-amino]-phenoxy}-acetate;

[4-[(2-guanidino-thiazole-4-carbonyl)-amino-phenoxy]-acetic acid hydrochloride;

ethyl {4-[(2-guanidino-thiazole-5-carbonyl)-amirio]-phenoxy}-acetate;

[4-[(2-guanidino-thiazole-5-carbonyl)-amino]-phenoxy]-acetic acid hydrochloride;

ethyl (4-{[2-(3-benzyl-ureido)-thiazole-4-carbonyl]-amino}-phenoxy)-acetate;

[4-[[2-(3-benzyl-ureido)-thiazole-4-carbonyl]-anmino]-phenoxy]-acetic acid;

ethyl (4-{[2-(3-benzyl-ureido)-thiazole-4-carbonyl]-amino}-2-methoxy-phenoxy)-acetate;

(4-{[2-(3-benzyl-ureido)-thiazole-4-carbonyl]-amino}-2-methoxy-phenoxy)-acetic acid;

ethoxycarbonylmethyl 5-{[2-(3-benzyl-ureido)-thiazole-4-carbonyl]-amino}-2-ethoxycarbonylmethoxy-benzoate;

5-{[2-(3-benzyl-ureido)-thiazole-4-carbonyl]-amino}-2-carboxymethoxy-benzoic acid;

ethyl (E)-3-[4-[[2-(3-benzyl-ureido)-thiazole-4-carbonyl]-amino]-phenyl]-acrylate;

(E)-3-[4-[2-(3-benzyl-ureido)-thiazole-4-carbonyl]-amino]-phenyl]-acrylic acid; and methyl [(4-{[2-(3-benzyl-ureido)-thiazole-4-carbonyl]-amino}-phenyl)-phenyl-amino]-acetate.

The following compounds are especially preferred examples of these:

Ethyl (4-{[2-(3-benzyl-ureido)-thiazole-4-carbonyl]-amino}-phenoxy)-acetate;

[4-[[2-(3-benzyl-ureido)-thiazole-4-carbonyl]-amino]-phenoxy]-acetic acid;

ethyl (4-{[2-(3-benzyl-ureido)-thiazole-4-carbonyl]-amino}-2-methoxy-phenoxy)-acetate;

(4-{[2-(3-benzyl-ureido)-thiazole-4-carbonyl]-amino}-2-methoxy-phenoxy)-acetic acid;

ethoxycarbonylmethyl 5-{[2-(3-benzyl-ureido)-thiazole-4-carbonyl]-amino}-2-ethoxycarbonylmethoxy-benzoate;

5-{[2-(3-benzyl-ureido)-thiazole-4-carbonyl]-amino}-2-carboxymethoxy-benzoic acid;

ethyl (E)-3-[4-[[2-(3-benzyl-ureido)-thiazole-4-carbonyl]-amino]-phenyl]-acrylate;

(E)-3-[4-[2-(3-benzyl-ureido)-thiazole-4-carbonyl]-amino]-phenyl]-acrylic acid.

Processes for the manufacture of compounds of formula I are also an object of the invention. The processes are based in each case on the reaction of a thiazole derivative, which represents the basic thiazole structure, with a reactive reagent, which represents the substituent $R^2$ or a reactive component and/or derivative thereof.

The following routes can be set out for the preparation of the corresponding basic thiazole structure, with the substituents and indices used in the following Schemes having the significances given above unless indicated otherwise.

Suitable basic thiazole structures can be prepared, for example, by the method presented in Scheme 1a. In this, an α-bromo-ketone of formula VII, such as ethyl pyruvate, is reacted in a solvent, such as ethanol, with a thiourea derivative of formula VIII, such as 2-imino-4-thiobiuret, at elevated temperature (J. Med. Chem. 1991, 34, 914). A subsequent saponification of the ester group by means of a base, such as aqueous NaOH or KOH, yields a thiazole-4-carboxylic acid derivative of type X (Scheme 1a).

In one process variant there is used an optionally substituted thiourea of formula IX, which, after cyclization to the thiazole, is reacted with an isocyanate, such as benzyl isocyanate, in a solvent, such as dimethylformamide (DMF), at room temperature, followed by a saponification of the ester as described above.

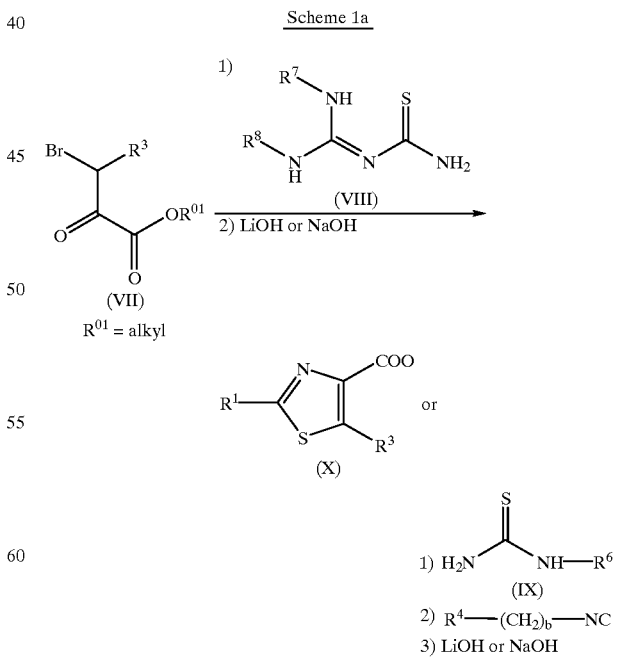

Scheme 1a

α-Halo-ketones are used in a further preparative process (Scheme 1b), which analogously to the process described above yields thiazole-5-carboxylic acid derivatives of type XIII (Farmaco 1989, 44, 1011). The α-halo-ketones of formula XII are prepared from the corresponding β-ketoesters (formula XI), such as ethyl butyrylacetate, ethyl pivaloyl-acetate, etc., by halogenation with e.g. bromine in a solvent, such as water, conveniently at a temperature of 0–5° C. (J. Chem. Soc. Perkin I, 1982, 162).

Scheme 1b

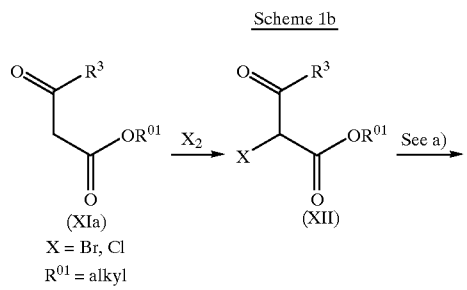

(XIa)    (XII)
X = Br, Cl
$R^{01}$ = alkyl

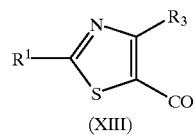

(XIII)

In another variant (Scheme 1c), the basic thiazole structure is synthesized by reaction of an N-protected amino acid thioamide, optionally substituted at the amino nitrogen, such as N-Boc-glycine thioamide (Boc as used herein signifies tert-butoxycarbonyl), with an α-halo-ketone of formula VII or XIb. A subsequent saponification of the ester group by means of a base, as described under Scheme 1a, yields thiazoleczirboxylic acid derivatives of formula XIV. After removal of the protecting group these can be further modified, for example in accordance with Scheme 7.

When a residue $((CH_2)_e$—NH—(protecting group)) is used in place of the $COOR^{01}$ residue in compound XIb or XII, then the aminothiazole derivatives corresponding to XIII can be obtained. The same also applies to Scheme 1a.

Scheme 1c

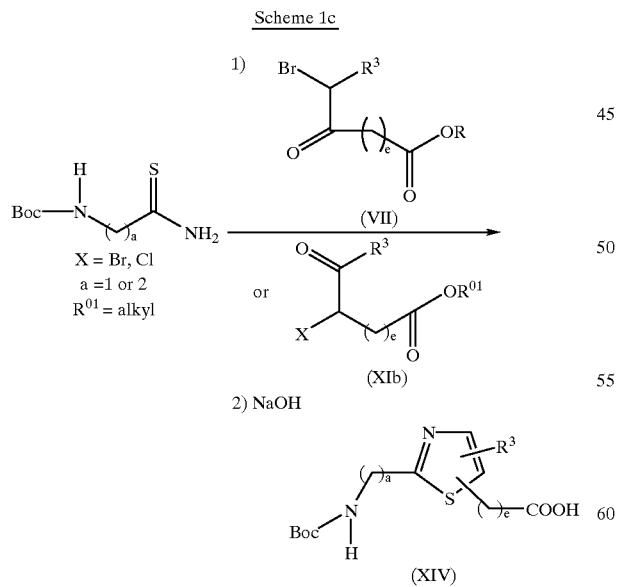

In an additional process variant (Scheme 1d), a substituted benzaldehyde, such as 3-nitrobenzaldehyde, or methyl 3-formylbenzoate, is converted with a nitroalkane, such as nitroethane, in a suitable solvent, such as acetic acid, with the addition of ammonium acetate, conveniently at elevated temperature, such as reflux temperature, into the corresponding nitro-olefin (Org. Synth. Coll. IV, 573 or Synthesis 1994, 258). This is epoxidized by means of an oxidation agent, such as hydrogen peroxide, in a suitable solvent, such as water, with the addition of aqueous sodium hydroxide solution to give a nitroepoxide of formula XV (Synthesis 1976, 53). The reaction of such a nitroepoxide with a thiourea derivative, such as 2-imino-4-thiobiuret, at elevated temperature, such as reflux temperature, yields arylthiazoles of formula XVI.

By using an alternative thiourea derivative in the above reaction and subsequent reaction with an isocyanate, such as benzyl isocyanate, in a solvent, such as DMF, at room temperature there are obtained arylthiazoles of formula XVII into which subsequently an additional substituent $R^5$ can be introduced by conventional methods.

Scheme 1d

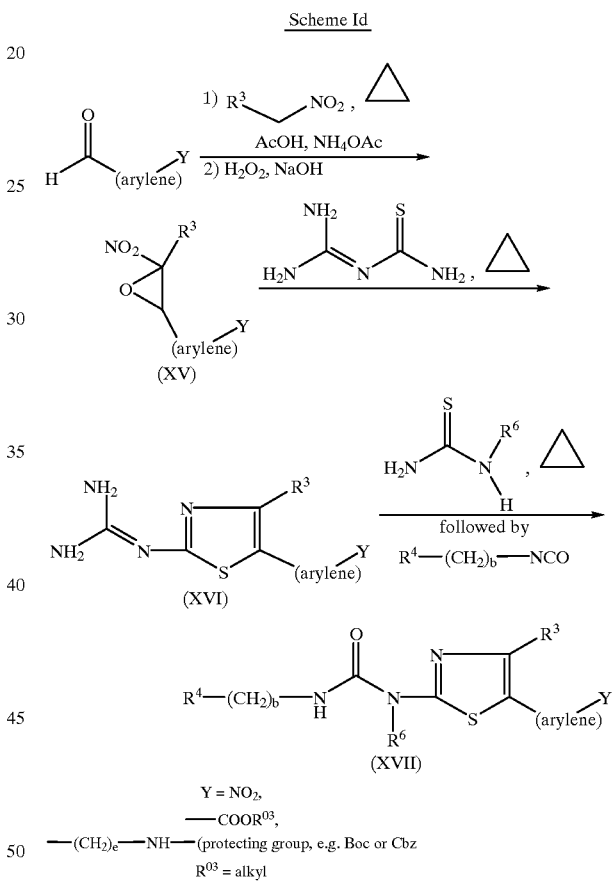

Y = $NO_2$,
—$COOR^{03}$,
—$(CH_2)_e$—NH—(protecting group, e.g. Boc or Cbz)
$R^{03}$ = alkyl When using in place of compound XV in Scheme 1d there is obtained the compound corresponding to XVI and XVII, but with the arylene residue being bonded to position 4 and $R^3$ being bonded to position 5 of the thiazole ring.

In order to prepare compounds analogous to XVI and XVII, with a being other than zero in accordance with formula (I), the thioamide used as the starting material in Scheme 1c can, for example, be used in place of the thiourea derivative used in Scheme 1d.

The basic thiazole structures obtainable in accordance with the above processes are converted in a subsequent reaction with reactive component and/or reactive derivative of the $R^2$ substituent to give a compound of formula I in one or more reaction steps.

When c is equal to 1, i.e. an amide bond is present on the thiazole structure, a corresponding thiazolecarboxylic acid can be reacted according to known methods with a corresponding amine to give a compound of formula I. In principle, the following route can be pursued:

In the following process variant (Scheme 2), the desired thiazole I is manufactured by coupling a thiazolecarboxylic acid of formula XVIII with an amine of formula XIX by means of BOP (BOP as used herein signifies (benzotiazole-1-yloxy)-tris-(dimethylamino)-phosphonium hexafluorophosphate)), HBTU (HBTU as used herein signifies O-(benzotriazol-1-yl)-N,N,N',N'-tetramethyluronium hexafluorophosphate) or CDMT (CDMT as used herein signifies 2-chloro-4,6-dimethoxy-1,3,5-triazine) and subsequently hydrolyzing the ester function. In this connection see also Z. J. Kaminski, Synthesis, 1987, 917.

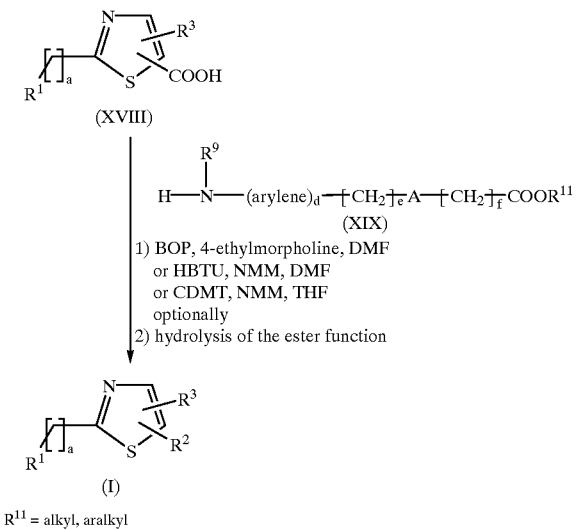

Where A is equal to —NH—, then this amine function has to be protected with usual protecting groups, e.g. Boc.

In particular, a thiazolecarboxylic acid XVIII is coupled with an amine of formula XIX by means of a conventional coupling reagent, such as HBTU, CDMT, etc., in the presence of a base, such as N-methylmorpholine, in a solvent, such as DMF or tetrahydrofuran (THF). The free compounds of formula I are formed in a subsequent ester cleavage by means of strong acid, such as trifluoroacetic acid in methylene chloride or aqueous hydrochloric acid, or by means of a strong base, such as NaOH.

Alternatively, the above compounds of formula I can also be obtained by reaction of a reactive partial component of the amnine XIX and subsequent addition of the still missing, substituent component of $R^2$.

Where c is equal to zero, i.e. the thiazole ring does riot carry an amide bond and d is 1, the following procedure is used for the synthesis of the compounds of formula I:

When e is also equal to zero, the basic thiazole structure is prepared analogously to Scheme 1d, with Y there being, equal to -O-benzyl (see Scheme 3).

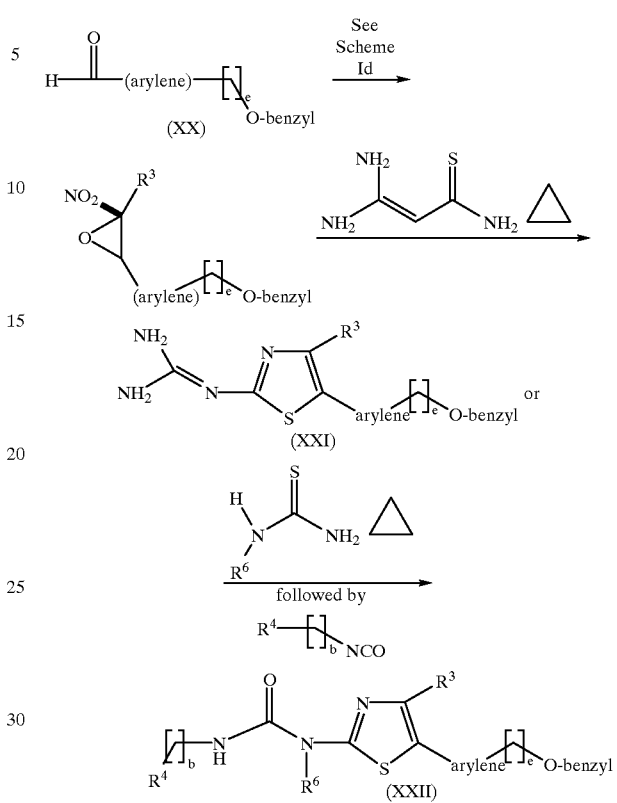

The benzyl group is cleaved off hydrogenolytically and, where A is oxygen, the resulting alcohol is reacted with the halide of formula XXIII

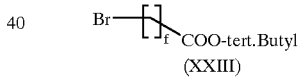

Where c is equal to zero, d is equal to 1, e is equal to zero and A is sulphur, the following procedure is used: The thiazole-arylene halide XXIV is reacted with the corresponding thiolate XXV e.g. in the presence of a Cu or Pd catalyst in DMF or DMSO.

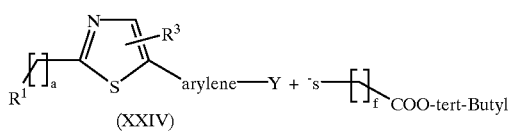

The halogenated arylene XXIV is prepared according to Scheme 1d, with Y being, bromine, chlorine or iodine.

Where c is equal to zero, d is equal to 1, e is other than zero and A is sulphur, the products from Scheme 3 are used. After hydrogenolytic cleaivage of the benzyl group (H₂, Pd/C) the thus-obtained alcohol is converted with e.g. methanesulphonyl chloride or p-toluenesulphonyl chloride into the corresponding mesylate or tosylate. Subsequently, reaction is then with the corresponding thiols or thiolates in the presence of a non-nucleophilic base e.g. dilsopropylethylamine.

Where c is equal to zero, d is equal to 1, e is equal to zero and A is equal to —NR$^{10}$—, the corresponding basic thiazole structures are prepared in accordance with Scheme 1d, with Y being equal to NO$_2$. The corresponding amine is obtained after reduction with hydrogen and aPd/C catalyst or Raney-nickel in alcohol.

Where R$^{10}$ is aralkyl, alkyl, cycloalkyl, heterocydlylalkyl or carboxyakyl, these are obtained by reductive amination with the corresponding aldehydes in the presence of borohydrides and catalytic hydrogenation (see e.g. G. Verardo et al., Synthesis 1993, 121).

Where R$^{10}$ is aryl or heteroaryl, the basic thiazole structure from Scheme 1d is used, with Y being equal to —NH$_2$. This is reacted with the corresponding heteroaryl halide or aryl halide (see J. P. Wolfe et al., Tetrahedron Letters, 1997, 38, 6367; S. L. Buchwald et al., Tetrahedron Letters, 1997, 38, 6359; S. L. Buchwald et al., J. Org. Chem., 1997, 62, 6066; D. Ma et al., Tetrahedron Asymm., 1998, 9, 1137).

The thus-obtained amines are then reacted with the corresponding halides of the formula

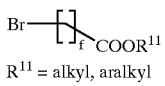

R$^{11}$ = alkyl, aralkyl under the conditions of a nucleophilic substitution reaction. The thus-obtained esters are cleaved under basic conditions, as mention ed in Scheme 1a.

Where R$^{10}$ is acyl or sulphonyl, the following procedure can be used:

Where d is zero, a protected amine of the following formula

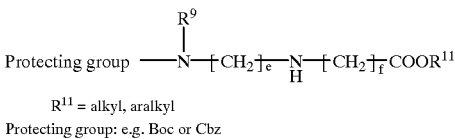

R$^{11}$ = alkyl, aralkyl
Protecting group: e.g. Boc or Cbz (see e.g. L. Christensen et al., Nucleic Acids Res., 1998, 26, 2735) is acylated at the free nitrogen atom with a carboxylic acid chloride or carboxylic acid anhydride or sulphonated with a sulphonic acid chloride (see e.g. I. S. Weitz et al., J. Org. Chem. 1997, 62, 2527 or P. H. H. Hermkens et al., Tetrahedron, 1988, 44, 1991). After cleavage of the protecting group the resulting amine can be coupled with a thiazolecarboxylic acid of formula X or XIII according to conventional methods and, after hydrolysis of the ester function, converted into the corresponding derivatives of formula I.

Where d is 1, a compound of the formula

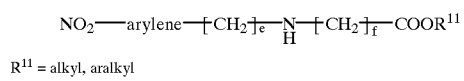

R$^{11}$ = alkyl, aralkyl (see J. Kihlberg et al., Acta Chem. Scand., Ser.B, 1983, B37, 911 and A. G. Katopodis et al., Biochemistry, 1990, 29, 4541) can be acylated or sulphonylated at the free nitrogen atom in the manner described above. The thus-obtained compounds are subsequently reduced to the corresponding amines of the formula

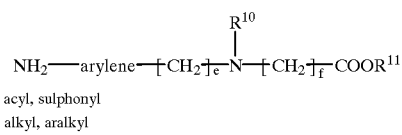

R$^{10}$ = acyl, sulphonyl
R$^{11}$ = alkyl, aralkyl

Where R$^9$ signifies alkyl or cycloalkyl, the thus-obtained amine is reacted with the corresponding aldehyde under the conditions of a reductive amination (procedure for the reductive amination e.g. see the case where c is equal to zero, d is equal to 1, e is equal to zero and A is equal to —NR$^{10}$—).

The corresponding derivatives of formula I can be obtained by coupling these amines with the thiazolecarboxylic acids of formula X or XIII and subsequent hydrolysis of the ester function.

Where c is equal to zero, d is equal to 1, e is other than zero and A is equal to —NR$^{10}$—, the compound corresponding to Scheme 1d with Y equal to O-benzyl is converted by hydrogenation into the corresponding alcohol [and] then reacted with e.g. methanesulphonyl chloride or paratoluenesulphonyl chloride to give the corresponding mesylate or tosylate. Subsequent reaction is with the corresponding amine components under the conditions of a nucleophilic substitution reaction.

The procedure in Scheme 4 is used for the preparation of the thiazole derivatives XXVI of formula I, with c being equal to zero, d being equal to 1, e being equal to zero and A being —CH=CH—:

Scheme 4

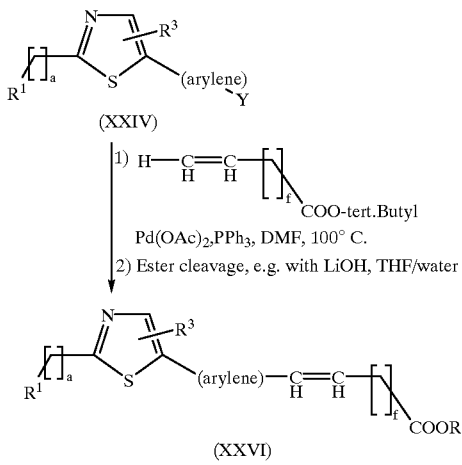

Y is equal to Br or I

The corresponding thiazole-arylene bromide or iodide XXIV is converted under the conditions of the Heck reaction in the presence of Pd/C in e.g. DMF at about 80° C. to 100° C. with the corresponding alkene (see e.g. S. G. Davies et al., J. Chem. Soc. Perkin 1, 1987, 2597).

Where c is equal to zero, d is equal to 1, e is 1 to 3 and A is —CH=CH—, the following procedure is used: The procedure as in Scheme 1d is followxed using the following aldehyde XXVII:

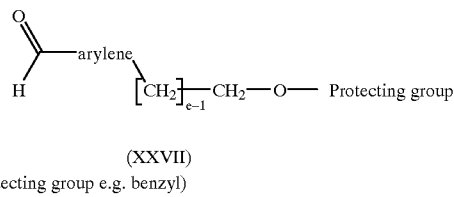

(XXVII)
(Protecting group e.g. benzyl)

The thus-obtained thiazole derivative (XXVIII) is now subsequently processed further in accordance with Scheme 5. The benzy protecting group is removed by catalytic hydrogdenation. The reductively obtained alcohol is finally oxidized to the aldehyde according to usual conditions (e.g. Tetrahedron Lett. 1992, 33, 5029).

Scheme 5

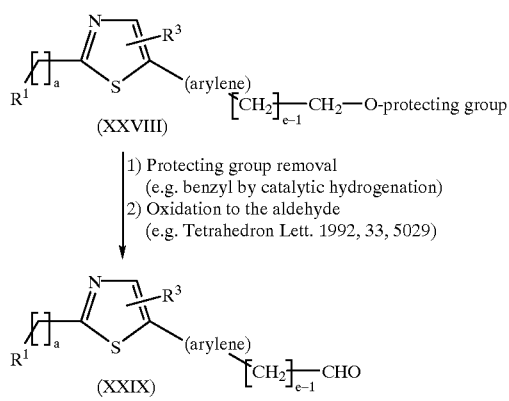

The thus-obtained aldehyde XXIX is reacted in accordance with Scheme 6 under Wittig conditions (or a variant thereof) with the phosphonium halide with the formation of the double bond. The free acid of the desired compound is obtained by ester cleavage e.g. LiOH/THF/H$_2$O.

Scheme 6

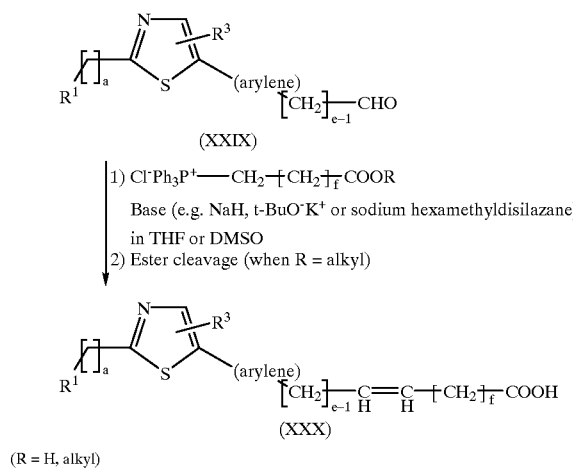

(R = H, alkyl)

In addition to the processes described above, the substituent R$^1$ can be varied in the scope of the definitions of formula I. For example, the Boc protecting group of compound (XIV) can be cleaved off for the preparation of the corresponding compounds of the formula

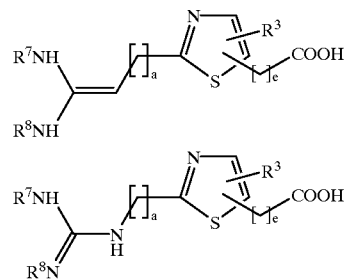

The resulting amine is reacted with the corresponding amidating reagent e.g. amidino-sulphonic acid to give the corresponding guanidine derivatives (R$^7$ and R$^8$ are hydrogen). Where R$^7$ and R$^8$ are other than hydrogen, an amidation procedure corresponding to M. A. Poss et al., Tetrahedron Letters, 1992, 33, 5933–36 is chosen.

In a process variant (Scheme 7), a thiazole derivative of formula XXXI can be guanidated (Tet. Lett 29, 3183–86, 1998) with intermediary protection of the acid functions contained in R$^2$ and R$^3$.

Scheme 7

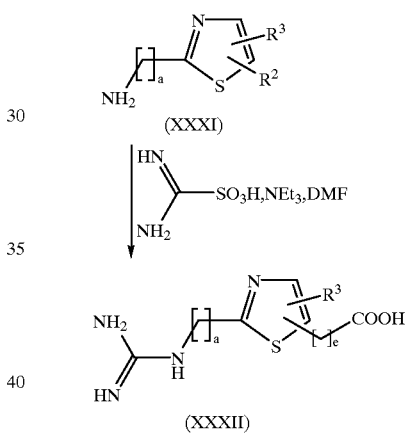

a = 1 or 2

Compound XXXI is reacted with an isocyanate for the manufacture of the corresponding urea derivatives.

Alternatively, the amine XXXI can also be treated with equimolar amounts of phosgene in the presence of a base e.g. triethylamine and this can then be reacted with the corresponding amine of the formula

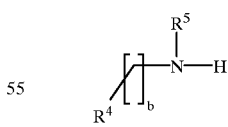

Where R$^6$ is other than hydrogen, after cleavage of the Boc protecting group from compound (XIV) alkylation by reductive amination with the corresponding aldehyde is carried out.

Compounds of the type XXXI can be obtained, for example, from compounds XIV by removal of the Boc protecting group under acidic conditions e.g. trifluoroacetic acid.

Alternatively, the thus-obtained amine can be converted stepwise into the corresponding monoalkylamines by reductive amination with the corresponding, aldehydes e.g. in the presence of borohydrides or H$_2$/PdC.

In order to obtain the corresponding heteroaryl derivatives of compound (XIV) there are used thiourea derivatives corresponding to Scheme 1c which are substituted on the nitrogen with heteroaryl. These are reacted with compound (VII) or (XIb).

Where a is equal to zero, the procedure starts from the corresponding basic thiazole compounds of Schemes 1a, 1b and 1d.

The amine XIX used in Scheme 2 can be prepared according to generally known processes. For example, the following procedure can be used when A is oxygen. The ether bond present can be obtained by reaction of a hydroxy function with the corresponding halide. At the same time, other reactive groups such as e.g. the amino function have to be inactivated using known protecting group technology.

Where A is sulphur, the thioether group can be prepared, for example, by reaction of a halide with the corresponding thiolate in DMF or DMSO. The thiolate used is produced from the corresponding thiol by abstraction of a proton by means of a base. In a variant, the desired thioether compound can be obtained by reaction of a thiolate with the corresponding mesylate or tosylate. This mesylate or tosylate can be obtained, for example, from the corresponding alcohols by reaction with methanesulphonyl chloride or paratoluenesulphonyl chloride.

Where A is —NR$^{10}$—, the desired nitrogen-carbon bond can be obtained according to the same principles as previously described (see c equal to zero and A is —NR$^{10}$—).

Where A is —CH=CH—, the amine used in Scheme 2 can be obtained in analogy to the previously described procedures (see Scheme 4, Scheme 5 and Scheme 6). Thus, e.g. analogously to Scheme 4 a corresponding aminobromoarylene or aminoiodoarylene can be reacted palladium-catalyzed with the corresponding alkene. In this case the amino group can carry a BOC, protecting group. Alternatively, the procedure can start from a corresponding nitrobromoarylene which, after the palladium-catalyzed coupling, is reduced with tin dichloride dihydrate in ethanol with the retention of the double bond. Likewise, the corresponding nitroarylene can be employed analogously to Scheme 5. After oxidation to the aldehyde and after performing the Wittig reaction the nitro group can then be reduced to the amine with tin (II) as described above.

The amine in which d is equal to zero required for Scheme 2 can be prepared starting from the corresponding protected aminoalcohol. After oxidation to the aldehyde (see Scheme 5) the desired amine is then obtained by a Wittig reaction.

The invention likewise embraces intermediates of the formula

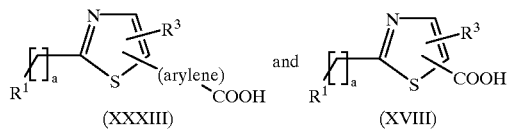

and their salts, with R$^1$, R$^3$ and a having the previously given significance and R$^3$ in formula XVIII not being hydrogen or methyl when R$^1$ is

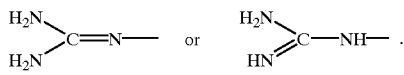

Especially preferred intermediates are:
Butyl (3-tert-butoxycarbonylamino-propoxy)-acetate;
butyl (3-amino-propoxy)-acetate hydrochloride;
ethoxycarbonylmethyl 5-benzyloxycarbonylamino-2-ethoxycarbonylmethoxy-benzoate;
ethoxycarbonylmethyl 5-amino-2-ethoxycarbonylmethoxy-benzoate.

The conversion of a compound of formula (I) into a pharmaceutical usable salt can be carried by treating such a compound with an inorganic acid, for example a hydrohalic acid, such as, for example, hydrochloric acid or hydrobromic acid, sulphuric acid, nitric acid, phosphoric acid etc., or with an organic acid, such as, for example, acetic acid, citric acid, maleic acid, fumaric acid, tartaric acid, methanesulphonic acid or p-toluenesulphonic acid.

The corresponding carboxylate salts of the compounds of formula (I) can also be manufactured by treatment with physiologically compatible bases.

The conversion of a compound of formula (I) into a pharmaceutically usable ester can be carried out by treating such a compound in the usual manner or as described in the Examples.

As mentioned previously, the compounds of formula I and their pharmaceutically usable salts and esters inhibit especially the binding of various adhesive proteins such as fibrinogen, vitronectin, von Willebrand factor, fibronectin, thrombospondin and osteopontin to the vitronectin receptors (such as e.g. $\alpha_v\beta_3$, $\alpha_v\beta_5$, $\alpha_v\beta_6$, $\alpha_v\beta_8$, etc.) on the surface of various types of cell. The compounds therefore influence cell-cell and cell-matrix interactions. Since the vitronectin receptors play a role, among other things, in the spread of tumor cells, in the new growth of vascular tissue, in the degradation of bon, tissue, in the migration of smooth muscle cells in vascular walls and in the penetration of virus particles into target cells, the compounds can be used as vitronectin receptor antagonists in the control or prevention of neoplasms, tumor metastasizing, osteoporosis, Paget's disease, diabetic retinopathy, macular degeneration, restenosis following vascular intervention, psoriasis, arthritis, kidney failure as well as infections caused by viruses, bacteria or fungi. Since the binding of adhesive proteins to the fibrinogen receptor ($\alpha_{IIb}\beta_3$) on the surface of blood platelets is practically not inhibited, undesired side effects such as e.g. bleeding can be suppressed with the therapeutic application of the said compounds.

The inhibition of the binding of adhesive proteins such as e.g. fibrinogen to vitronectin receptors (such as e.g. $\alpha_v\beta_3$, $\alpha_v\beta_5$, $\alpha_v\beta_6$, $\alpha_v\beta_8$, etc. or to the fibrinogen receptor ($\alpha_{IIb}\beta_3$) by compounds of formula (I) can be determined as described by L. Alig et al. (J.Med.Chem. 1992, 35, 4393–4407).

In detail thereto, the wells of microtiter plates (Nunc-Immunoplate MaxiSorp) were coated overnight at 4° C. with the vitronectin receptor $\alpha_v\beta_3$ (from human placenta, 100 µl/well) in a buffer system with 150 mmol/l NaCl, 1 mmol/CaCl$_2$, 1 mmol/l MgCl$_2$, 0.0005% Triton X-100 and 20 mmol/l Tris HCl, pH 7.4. The non-specific binding sites were blocked by incubation with 3.5% bovine serum albumin (BSA from Fluka) at 20° C. for at least 1 h. Before the beginning of the test the plates were washed in each case once with 150 mmol/l NaCl, 1 mmol/l CaCl$_2$, 1 mmol/l MgCl$_2$ and 20 mmol/l Tris HCl, pH 7.4 (buffer A). The thus-coated plates can be stored for at least 2 months in the presence of 0.05% $NaN_3$ (in buffer A) at 4° C. in a humidity chamber without loss of binding activity. Fibrinogen (IMCO, free from fibronectin) was diluted to 1.5 μg/ml in buffer A in the presence of 1% BSA. The wells coated with the receptor were incubated with fibrinogen (100 μl/well) overnight at room temperature in the absence of or in the presence of increasing concentrations of RGDS (as the reference substance, H-Arg-Gly-Asp-Ser-OH) or the compounds to be measured. Non-bound fibrinogen was removed by three-fold washing with buffer A, bound fibrinogen was detected by an enzyme linked immunosorbent assay (ELISA) procedure. Antibodies of rabbits directed against human fibrinogen (Dakopatts, Denmark), diluted in buffer A in the presence of 0.1% BSA, were added at room temperature for 1 h., followed by incubation with biotinylated antibodies directed against rabbit immunoglobulin (Amersham) for 30 min. Non-bound antibodies were removed by three-fold washing with buffer A. Thereafter, the pre-formed streptavidin-biotinylated peroxidase complex (Amersham) was added for 30 min. Three-fold washing with buffer A was again carried out. After addition of the peroxidase substrate ABTS (2,2'-azino-bis(3-ethylbenzothiazoline-6-sulphonic acid), Boehringer Mannheim) the enzyme activity was measured with a multichannel photometer (UVmax, Molecular Devices). The difference between total binding activity (in the absence of a test substance) and non-specific binding activity (in the presence of 100 μM RGDS) is taken as the specific binding activity. The concentration of a test substance which is required to inhibit the specific binding activity by 50% was defined as the $IC_{50}$.

The isolation of the receptor $a_vb_3$ used in the test can be carried out as follows: Human placenta is stored at −80° C. immediately after its excision. In order to extract the receptor, each placenta is superficially thawed and cut into narrow strips with a scalpel. The pieces are washed twice with a buffer of 150 mmol/l NaCl, 1 mmol/l $CaCl_2$, 1 mmol/l $MgCl_2$ and 20 mmol/l Tris HCl (pH 7.4). The proteins are extracted at room temperature for one hour with a buffer solution from 1% Triton X-100, 150 mmol/l NaCl, 1 mmol/l $CaCl_2$, 1 mmol/l $MgCl_2$, 20 mmol/l Tris HCl, 0.02% $NaN_3$, 0.5 mmol/l phenylmethane-sulphonyl fluoride, 1 mmol/l leupeptin and 2 mmol/l N-ethylmaleimide (pH 7.4) and filtered through sterile gauze. The filtrate is centrifuged at 30000 g for 30 min. at 4° C. The glycoproteins are firstly separated with the aid of a concanavalin A-Sepharose 4B column. The proteins bound to the column are eluted and then added to a Aeg-RGDS column. After repeated washing the bound vitronectin receptor is eluted by 3 mmol/l RGDS in a buffer of 0.1% Triton X-100, 150 mmol/l NaCl, 20 mmol/l Tris HCl, 1 mmol/l $CaCl_2$, 1 mmol/l $MgCl_2$, 0.05% $NaN_3$ (pH 7.0).

The results obtained in the foregoing test using representative compounds of formula I as the test compound are compiled in the following Table.

TABLE 1

| Substance | VNR $IC_{50}$ [nM] |
| --- | --- |
| (4-{[2-(3-benzyl-ureido)-thiazole-4-carbonyl]-amino}-2-methoxy-phenoxy)-acetic acid | 0.2 |
| 5-{[2-(3-benzyl-ureido)-thiazole-4-carbonyl]-amino}-2-carboxymethoxy-benzoic acid | 1.3 |
| (4-((2-(3-benzyl-ureido)-thiazole-4-carbonyl)-amino)-phenoxy)-acetic acid | 1.0 |

Preferred compounds have an $IC_{50}$ value which is below 100 nM; especially preferred compounds have a value below 10 nM. Particularly preferred compounds have an $IC_{50}$ value which is below 2 nM.

The compounds of formula I and their pharmaceutically usable salts and esters can be used as medicaments (e.g. in the form of pharmaceutical preparations). The pharmaceutical preparations can be administered internally such as orally (e.g. in the form of tablets, coated tablets, dragees, hard and soft gelatine capsules, solutions, emulsions or suspensions), nasally (e.g. in the form of nasal sprays) or rectally (e.g. in the form of suppositories). The administration can, however, also be effected parentally such as intramuscularly or intravenously (e.g. in the form of injection solutions).

The compounds of formula I and their pharmaceutically usable salts and esters can be processed with pharmaceutically inert, inorganic or organic adjuvants for the production of tablets, coated tablets, dragees and hard gelatine capsules. Lactose, corn starch or derivatives thereof, talc, stearic acid or its salts etc. can be used, for example, as such adjuvants for tablets, dragees and hard gelatine capsules.

Suitable adjuvant for soft gelatine capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutical usable salts and esters can be used as vitronectin receptor antagonists, especially for the treatment or prophylaxis of neoplasms, tumor metastasizing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi. The dosage can vary in wide limits and will, of course by fitted to the individual requirements in each particular case. In the case of oral administration a daily dosage of about 0.1 mg to 20 mg per kg body weight, preferably about 0.5 mg to about 4 mg per kg body weight (e.g. approximately 300 mg per person), divided into preferably 1–3 individual doses, which can consist, for example, of the same amounts, should in general be adequate. It will, however, be clear that the upper limit given above can be exceeded when it is established that this is indicated.

The invention is illustrated hereinafter by Examples, which do not limit the invention.

EXAMPLE 1

175 mg of 2-guanidino-4-methyl-thiazole-5-carboxylic acid, 2.6 ml of DMF, 0.29 ml of N-MM and 332 mg of HBTU are stirred at room temperature (RT) for one hour, treated with 197 mg of butyl (3-amino-propoxy)-acetate hydrochloride and stirred at RT for a further 18 hrs. For the working up, the mixture is diluted with ethyl acetate, washed with dilute sodium carbonate solution, dilute sodium chloride solution and saturated sodium chloride solution, dried and evaporated in a vacuum. Chromatography on silica gel with methylene chloride-alcohol gives 162 mg of butyl {3-[(2-guanidino-4-methyl-thiazole-5-carbonyl)-amino]-propoxy}-acetate, mass spectroscopy (MS): 372 (M+H)$^+$.

The butyl (3-amino-propoxy)-acetate hydrochloride can be prepared as follows:
a) Butyl 2-cyano-ethoxyacetate is hydrogenated on Pd/C in acetic acid and subsequently reacted in tert-butanol and triethylamine with di-tert-butyl dicarbonate to give butyl (3-tert-butoxycarbonylamino-propoxy)-acetate and purified by chromatography; MS: 290 (M+H)$^+$.
b) By treatment with 4N HCl in ethyl acetate there is obtained therefrom butyl (3-amino-propoxy)-acetate hydrochloride, melting point (m.p.) 36–36° C., MS: 190 (M+H)$^+$.

EXAMPLE 2

151 mg of butyl {3-[(2-guanidino-4-methyl-thiazole-5-carbonyl)-amino]-propoxy}-acetate are stirred for 5 hrs. in 3 ml of 25% hydrochloric acid. The reaction mixture is evaporated to dryness in a vacuum and the residue is lyophilized from acetic acid. There are obtained 144 mg of [3-[(2-guanidino-4-methyl-thiazole-5-carbonyl)-amino]-propoxy]-acetic acid hydrochloride (1:1), m.p. 48–51° C., MS: 316 (M+H)$^+$.

EXAMPLE 3

400 mg of 2-guanidino-4-methyl-thiazole-5-carboxylic acid, 463 mg of ethyl 4-amino-phenyloxyacetate hydrochloride, 6 ml of DMF, 0.67 ml of N-MM and 759 mg of HBTU are stirred at RT for 22 hrs. The working up and purification are effected as described in Example 1. Crystallization from acetonitrile (MeCN) gives 368 mg of ethyl {4-[(2-guanidino-4-methyl-thiazole-5-carbonyl)-amino]-phenoxy}-acetate, m.p. 223° C.;, MS: 378 (M+H)$^+$.

EXAMPLE 4

330 mg of ethyl {4-[(2-guanidino-4-methyl-thiazole-5-carbonyl)-amino]-phenoxy}-acetate are stirred at RT for 11 hrs. in 6 ml of 25% hydrochloric acid. The reaction mixture is evaporated to dryness in a vacuum and the residue is trituraited in MeCN. There are obtained 293 mg of [4-[(2-guanidino-4-methyl-thiazole-5-carbonyl)-amino]-phenoxy]-acetic acid hydrochloride (1:1); m.p. 273° C., MS: 350 (M+H)$^+$.

EXAMPLE 5

2-Guanidino-4-methyl-thiazole-5-carboxylic acid is reacted with tert-butyl (3-amino-phenoxy)-acetate in the same manner as in Example 3. Chromatography on silica gel with methylene chloride-ethyl acetate and methylene chloride-alcohol gives 176 mg of tert-butyl {3-[(2-guanidino-4-methyl-thiazole-5-carbonyl)-amino]-phenoxy}-acetate, m.p. 204° C., MS: 406 (M+H)$^+$.

EXAMPLE 6

142 mg of tert-butyl {3-[(2-guanidino-4-methyl-thiazole-5-carbonyl)-amino]-phenoxy}-acetate is stirred in 1.1 ml of methylene chloride and 1.1 ml of trifluoroacetic acid (TFA) for 2 hrs. at RT. The reaction mixture is evaporated in a vacuum, the residue is taken up in water and the solution is evaporated to dryness. The solid is suspended in water, adjusted to pH 8 with 1N ammonia while stirring, filtered off under suction, washed with water and dried. There are obtained 101 mg of [3-[(2-guanidino-4-methyl-thiazole-5-carbonyl)-amino]-phenoxy]-acetic acid, m.p. 284° C., MS: 350 (M+H)$^+$.

EXAMPLE 7

In the same manner as described in Example 3, from 2-guanidino-thiazole-4-carboxylic acid and ethyl 4-amino-phenyloxyacetate hydrochloride there is obtained ethyl {4-[(2-guanidino-thiazole-4-carbonyl)-amino]-phenoxy}-acetate, m.p. 206° C., MS: 364 (M+H)$^+$.

EXAMPLE 8

227 mg of ethyl {4-[(2-guanidino-thiazole-4-carbonyl)-amino]-phenoxy}-acetate are stirred for 3 days at RT in 25% hydrochloric acid. The precipitate is filtered off under suction, washed with water, triturated in methanol, filtered off under suction and dried. There are obtained 165 mg of [4-[(2-guanidino-thiazole-4-carbonyl)- amino]-phenoxy]-acetic acid hydrochloride (1:1); m.p. 278° C., MS: 336 (M+H)$^+$.

EXAMPLE 9

In the same manner as described in Example 3 and crystallization from methanol (MeOH), from 2-guanidino-thiazole-5-carboxylic acid and ethyl 4-amino-phenyloxyacetate hydrochloride there is obtained ethyl {4-[(2-guanidino-thiazole-5-carbonyl)-amino]-phenoxy}-acetate, m.p. 218° C., MS: 364 (M+H)$^+$.

EXAMPLE 10

239 mg of ethyl {4-[(2-guanidino-thiazole-5-carbonyl)-amino]-phenoxy}-acetate are stirred for 27 hrs. in 4.8 ml of 25% hydrochloric acid. The precipitate is filtered off under suction, washed with water and dried. There are obtained 222 mg of [4-[(2-guanidino-thiazole-5-carbonyl)-amino]-phenoxy]-acetic acid hydrochloride (1:1), m.p. 336° C., MS: 364 (M+H)$^+$.

EXAMPLE 11

419 mg of 2-(3-benzyl-ureido)-thiazole-4-carboxylic acid, 265 mg of CDMT, 4.5 ml of THF and 0.18 ml of N-MM are 4.5 hrs. at RT. After the addition of 350 mg of ethyl 4-amino-phenyloxyacetate hydrochloride and 0.18 ml of N-MM the mixture is stirred for a further 20 hrs. at RT. For the working up, the mixture is diluted with ethyl acetate and washed in succession with dilute hydrochloric acid, water, dilute sodium carbonate solution, water and saturated sodium chloride solution, dried over sodium sulphate and evaporated in a vacuum. Chromatography on silica gel with methylene chloride-alcohol 99:1 and crystallization from ether gives 350 mg of ethyl (4-{[2-(3-benzyl-ureido)-thiazole-4-carbonyl]-amino}-phenoxy)-acetate, m.p. 173° C., MS: 455 (M+H)$^+$.

EXAMPLE 12

243 mg of ethyl (4-{[2-(3-benzyl-ureido)-thiazole-4-carbonyl]-amino}-phenoxy)-acetate are stirred in 4.3 ml of ethanol and 0.8 ml of 1N NaOH for 4.5 hrs. at RT. For the working up, the mixture is stirred into ethyl acetate/dilute hydrochloric acid, the organic phase is separated, washed with water and sodium chloride solution, dried over sodium sulphate dried and evaporated in a vacuum. Crystallization from ether gives 208 mg of [4-[[2-(3-benzyl-ureido)-thiazole-4-carbonyl]-amino]-phenoxy]-acetic acid, m.p. 208° C., MS: 427 (M+H)$^+$.

EXAMPLE 13

Analogously to Example 11, from 2-(3-benzyl-ureido)-thiazole-4-carboxylic acid and ethyl (4-amino-2-methoxyphenoxy)-acetate there is obtained ethyl (4-{[2-(3-benzyl-ureido)-thiazole-4-carbonyl]-amino}-2-methoxy-phenoxy)-acetate, m.p. 197–198° C., MS: 485 (M+H)$^+$.

EXAMPLE 14

In the same manner as described in Example 12 and crystallization from acetonitrile, from ethyl (4-{[2-(3-benzyl-ureido)-thiazole-4-carbonyl]-amino}-2-methoxy-phenoxy)-acetate there is obtained (4-{[2-(3-benzyl-ureido)-thiazole-4-carbonyl]-amino}-2-methoxy-phenoxy)-acetic acid, m.p. 210° C., MS: 457 (M+H)$^+$.

EXAMPLE 15

Analogously to Example 11, from 2-(3-benzyl-ureido)-thiazole-4-carboxylic acid and ethoxycarbonylmethyl 5-amino-2-ethoxycarbonylmethoxy-benzoate there is obtained ethoxycarbonylmethyl 5-{[2-(3-benzyl-ureido)-thiazole-4-carbonyl]-amino}-2-ethoxycarbonylmethoxy-benzoate, m.p. 125–127° C. (from ethyl acetate), MS: 585 (M+H)$^+$.

The starting material can be prepared as follows:
a) 5-Benzyloxycarbonylamino-2-hydroxy-benzoic acid is reacted at reflux in acetone with ethyl bromoacetate in the presence of potassium carbonate to give ethoxycarbonylmethyl 5-benzyloxycarbonylamino-2-ethoxycarbonylmethoxy-benzoate, m.p. 77–78° C., MS: 460 (M+H)$^+$.
b) By catalytic hydrogenation on Pd/C in ethanol (EtOH) there is obtained therefrom ethoxycarbonylmethyl 5-amino-2-ethoxycarbonylmethoxy-benzoate, MS: 326 (M+H)$^+$.

EXAMPLE 16

378 mg of ethoxycarbonylmethyl 5-{[2-(3-benzyl-ureido)-thiazole-4-carbonyl]-amino}-2-ethoxycarbonylmethoxy-benzoate, 6.5 ml of ethanol and 1.29 ml of 2N sodium hydroxide solution are stirred for 5 hrs. at RT. After the addition of 3 ml of acetic acid and 2 ml of water the mixture is warmed until a homogeneous solution is obtained. After cooling the precipitate is filtered off under suction, washed with acetic acid-water 1:1 and dried. There are obtained 290 mg of 5-{[2-(3-benzyl-ureido)-thiazole-4-carbonyl]-amino}-2-carboxymethoxy-benzoic acid, m.p. 219° C., MS: 471 (M+H)$^+$.

EXAMPLE 17

2-(3-Benzyl-ureido)-thiazole-4-carboxylic acid is coupled with ethyl (E)-3-(4-amino-phenyl)-acrylate in analogy to Example 11 After chromatography on silica gel with methylene chloride-ethanol 98:2 and crystallization from ether there is obtained ethyl (E)-3-[4-[[2-(3-benzyl-ureido)-thiazole-4-carbonyl]-amino]-phenyl]-acrylate, m.p. 207° C., MS: 451 (M+H)$^+$.

EXAMPLE 18

235 mg of ethyl (E)-3-[4-[[2-(3-benzyl-ureido)-thiazole-4-carbonyl]-amino]-phenyl]-acrylate, 4.7 ml of ethanol and 1 ml of 2N NaOH are stirred for 6 hrs. at RT. The reaction mixture is diluted with 4.7 ml of water and adjusted to pH 2 with 2 ml of 1N hydrochloric acid. The precipitate is filtered off under suction, washed with water, triturated in ethanol, filtered off under suction and dried. There are obtained 164 mg of (E)-3-[4-[2-(3-benzyl-ureido)-thiazole-4-carbonyl]-amino]-phenyl]-acrylic acid, ra.p. 264° C., MS: 423 (M+H)$^+$.

EXAMPLE 19

A solution of 1.1 g (4 mmol) of 2-(3-benzyl-ureido)-thiazole-4-carboxylic acid, 1.05 g (4 mmol) of methyl [(4-amino-phenyl)-phenyl-amino]-acetate, 1.7 g (4.4 mmol) of HTBU and 0.6 ml (6 mmol) of N-methylmorpholine (NMM) in 50 ml of DMF is stirred at room temperature overnight. After the usual working up followed by chromatography (silica gel, dichloromethane/methanol 30:1) there are obtained 1.2 g of methyl [4-{[2-(3-benzyl-ureido)-thiazole-4-carbonyl]-amino}-phenyl)-phenyl-amino]-acetate in the form of an amorphous powder. MS: 516 (M+1).

The starting material can be prepared as follows:
a) 4-Nitro-diphenylamine (Aldrich) is reacted with methyl bromoacetate in the presence of potassium carbonate in DMF at 70° C. to give methyl [(4-nitro-phenyl)-phenyl-amino]-acetate (brown oil). MS: 287 (M+1).
b) By catalytic hydrogenation of methyl [(4-nitro-phenyl)-phenyl-amino]-acetate in methanol in the presence of palladium/carbon (10%) there is obtained, after filtration and removal of the solvent, methyl [(4-amino-phenyl)-phenyl-amino]-acetate in the form of a brown oil. MS: 256 (M+).

EXAMPLE A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of formula I can be used in a manner known per se as the active ingredient for the production capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Upon reading the present specification, various alternative embodiments will become obvious to the skilled artisan. These variations are to be considered within the scope and spirit of the subject invention, which is only to be limited by the claims that follow and their reasonable equivalents.

What is claimed is:

1. A compound of formula:

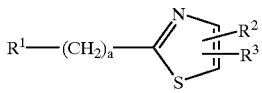
(I)

wherein
$R^1$ is

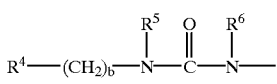

or

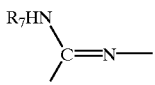

or

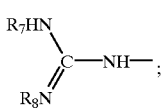

$R^2$ is

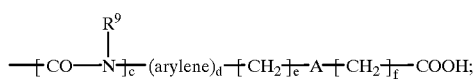
(II)

$R^3$ is hydrogen, alkyl, cycloalkyl, aryl, aralkyl, heteroaryl, carboxy, alkyl-O—CO— or aralkyl-O—CO—;

$R^4$ is hydrogen, alkyl, cycloalkyl, aryl or heteroaryl;

$R^5$ and $R^6$, independent of one another, are hydrogen, alkyl, cycloalkyl or heteroaryl;

$R^7$ and $R^8$, independent of one another, are hydrogen, alkyl, cycloalkyl or heteroaryl or $R^7$ and $R^8$ together with the N atoms to which they are attached form a 5- to 8-membered heterocyclic or a 5- to 8-membered ring substituted with one or more alkyl substituents;

$R^9$ is hydrogen, alkyl or cycloalkyl;

$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl CO—, alkylsulphonyl, arylsulphonyl or heteroarylsulphonyl;

A is oxygen, sulphur, —CH=CH— or 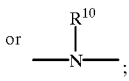;

a to f are zero or whole positive integers, with a being zero to 2; b being zero to 4; c and d being zero or 1, with the proviso that c and d are not both simultaneously zero; e is zero to 5, with the proviso that e is other than zero when d is zero and e is zero to 3 when A is equal to —CH=CH—; and f is zero to 3, with the proviso that f is not zero when A is oxygen, sulphur or

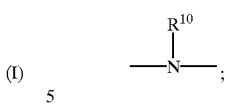;

and their pharmaceutically usable salts and esters.

2. The compound in accordance with claim 1, wherein $R^2$ is

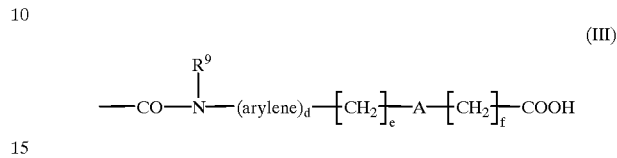
(III)

wherein
$R^9$ is hydrogen, alkyl or cycloalkyl;
A is oxygen, sulphur, —CH=CH— or 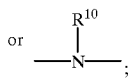;

$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, arylsulphonyl or heteroarylsulphonyl;

d is zero or 1, e is an integer from zero to 5, with the proviso that e is other than zero when d is zero, and e is an integer from zero to 3 when A is equal to —CH=CH—; and f is and integer from zero to 3, with the proviso that f is not zero when A is oxygen, sulphur or

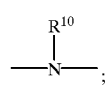;

and their pharmaceutically usable salts and esters.

3. The compound in accordance with claim 2, wherein $R^2$ is

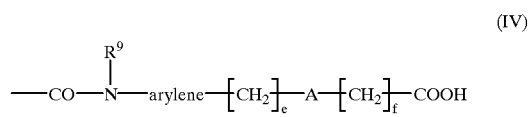
(IV)

wherein
$R^9$ is hydrogen, allkyl or cycloalkyl;
A is oxygen, sulphur, —CH=CH— or 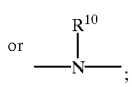;

$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, arylsulphonyl or heteroarylsulphonyl;

e is an integer from zero to 5, and e is an integer from zero lo 3 when A is equal to —CH=CH—; and f is and integer from zero to 3, with the proviso that f is not zero when A is oxygen, sulphur or

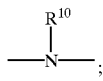

and their pharmaceutically usable salts and esters.

4. The compound in accordance with claim 3, wherein $R^2$ is

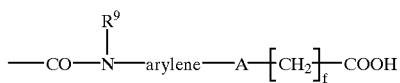 (V)

and $R^9$, A and f are $R^9$ is hydrogen, alkyl or cycloalkyl;

A is oxygen, sulphur, —CH=CH— or 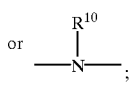

$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, arylsulphonyl or heteroarylsulphonyl;

f is an integer from zero to 3, with the proviso that f is not zero when A is oxygen or sulphur; and their pharmaceutically usable salts and esters.

5. The compound in accordance with claim 2, wherein $R^2$ is

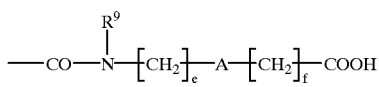 (VI)

wherein $R^9$ is hydrogen, alkyl or cycloalkyl;

A is oxygen, sulphur, —CH=CH— or 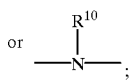

$R^{10}$ is hydrogen, aryl, aralkyl, heteroaryl, heterocyclylalkyl, carboxyalkyl, alkyl, cycloalkyl, alkyl-O—CO—, aralkyl-O—CO—, alkyl-CO—, alkylsulphonyl, arylsulphonyl or heteroarylsulphonyl;

e is an integer from zero to 5, and e is an integer from zero to 3 when A is equal to —CH=CH—; and f is and integer from zero to 3, with the proviso that f is not zero when A is oxygen, sulphur or

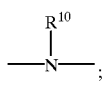

and their pharmaceutically usable salts and esters.

6. The compound in accordance with claim 1, wherein A is oxygen or —CH=CH—.

7. The compound in accordance with claim 1, wherein $R^1$ is

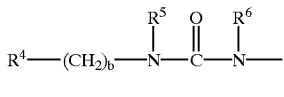

wherein $R^4$ is hydrogen, alkyl, cycloalkyl, aryl or heteroaryl;

$R^5$ and $R^6$ independently of one another are hydrogen, alkyl, cycloalkyl or heteroaryl; and b is an integer from zero to 4.

8. The compound in accordance with claim 1, wherein arylene is phenylene or substituted phenylene having one or more alkoxy, aralkoxy, halogen, alkoxy-alkoxy, carboxy or

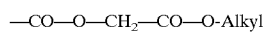

substituents.

9. The compound in accordance with claim 8, in which arylene is meta- or para-phenylene or substituted meta- or para-phenylene, with the substituents of the phenylene previously given by $R^2$ standing meta- or para- to one another and with the substituted phenylene carrying on the ring an additional substituent selected from the group of alkoxy, carboxy or

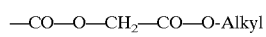

10. The compound in accordance with claim 1, wherein $R^3$ is hydrogen, alkyl, cycloalkyl or phenyl.

11. The compound in accordance with claim 1, wherein $R^4$ is hydrogen, alkyl, cycloalkyl or phenyl.

12. The compound in accordance with claim 1, wherein $R^5$, $R^6$, $R^7$ and $R^8$ are hydrogen or $R^5$ and $R^6$ are both hydrogen and $R^7$ and $R^8$ together with the N atoms to which they are attached form a 5- to 6-membered ring.

13. The compound in accordance with claim 1, wherein $R^9$ is hydrogen or cycloalkyl.

14. The compound in accordance with claim 1, wherein $R^2$ is attached to position 4 and $R^3$ is attached to position 5 of the thiazole ring.

15. A compound of the formula:

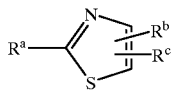

wherein, $R^a$ is

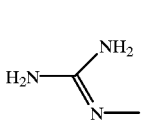 or 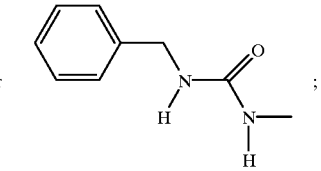 ;

$R^b$ is

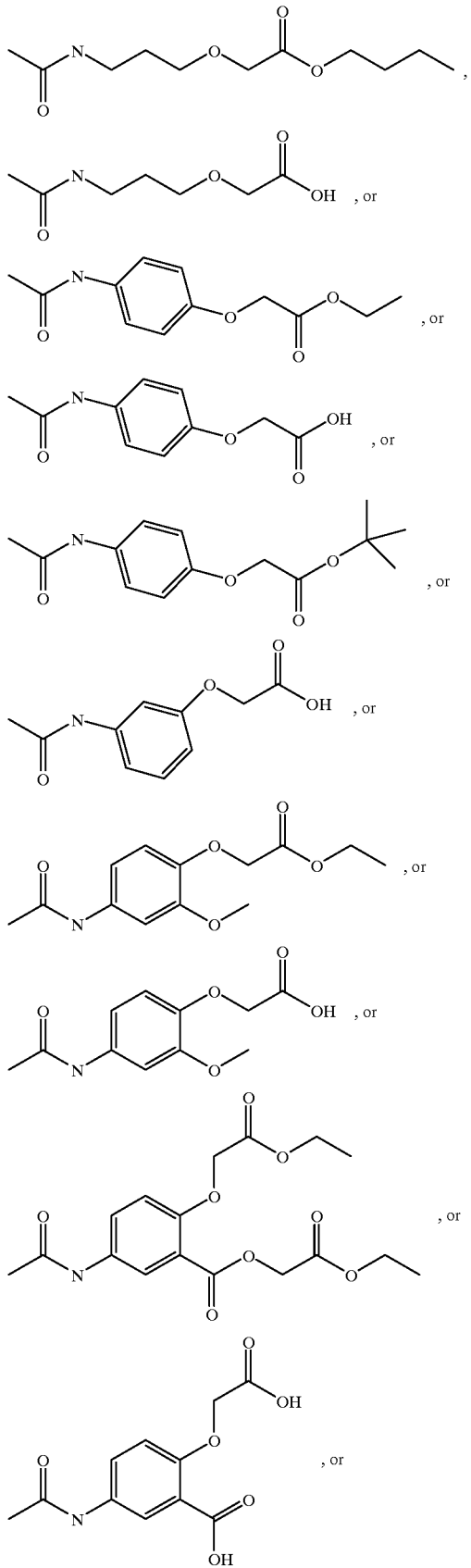

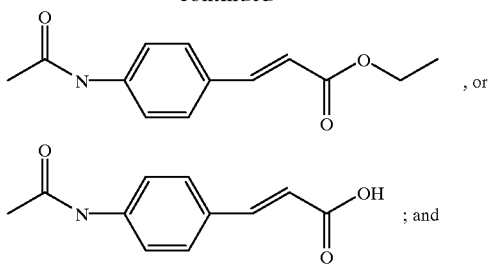

$R^c$ is hydrogen or methyl.

16. The compound of claim 15, wherein $R^a$ is

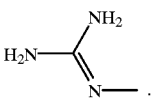

17. The compound of claim 16, wherein $R^b$ is

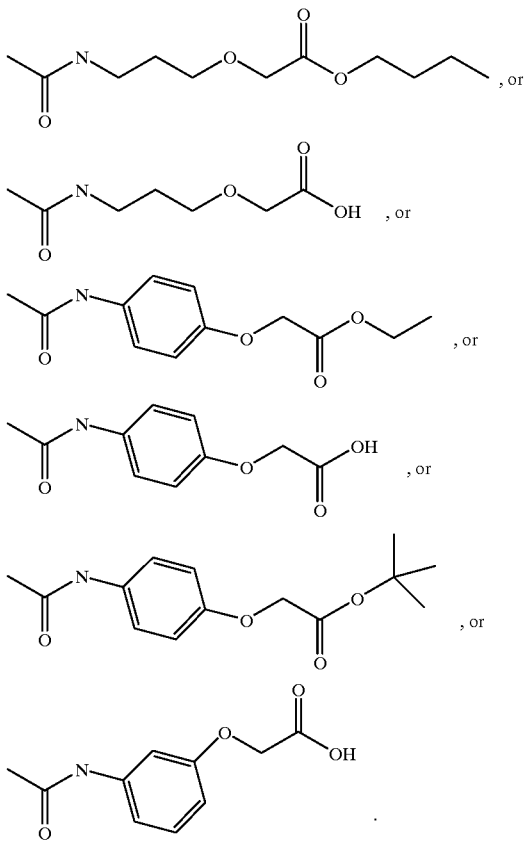

18. The compound of claim 17, wherein $R^c$ is methyl.

19. The compound of claim 18, which is butyl {3-[(2-guanidino-4-methyl-thiazole-5-carbonyl)-amino]-propoxy}-acetate.

20. The compound of claim 18, which is [3-[(2-guanidino-4-methyl-thiazole-5-carbonyl)-amino]-propoxy]-acetic acid hydrochloride.

21. The compound of claim 18, which is ethyl {4-[(2-guanidino-4-methyl-thiazole-5-carbonyl)-amino]-phenoxy}-acetate.

22. The compound of claim 18, which is [4-[(2-guanidino-4-methyl-thiazole-5-carbonyl)-amino]-phenoxy]-acetic acid hydrochloride.

23. The compound of claim 18, which is tert-butyl {3-[(2-guanidino-4-methyl-thiazole-5-carbonyl)-amino]-phenoxy}-acetate.

24. The compound of claim 18, which is [3-[(2-guanidino-4-methyl-thiazole-5-carbonyl)-amino]-phenoxy]-acetic acid.

25. The compound of claim 17, wherein $R^c$ is hydrogen.

26. The compound of claim 25, which is ethyl {4-[(2-guanidino-thiazole-4-carbonyl)-amino]-phenoxy}-acetate.

27. The compound of claim 25, which is [4-[(2-guanidino-thiazole-4-carbonyl)-amino]-phenoxy]-acetic acid hydrochloride.

28. The compound of claim 25, which is ethyl {4-[(2-guanidino-thiazole-5-carbonyl)-amino]-phenoxy}-acetate.

29. The compound of claim 25, which is [4-[(2-guanidino-thiazole-5-carbonyl)-amino]-phenoxy]-acetic acid hydrochloride.

30. The compound of claim 15, wherein $R^a$ is

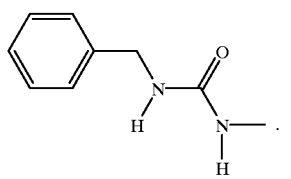

31. The compound of claim 30, wherein $R^c$ is hydrogen.

32. The compound of claim 31, wherein $R^b$ is

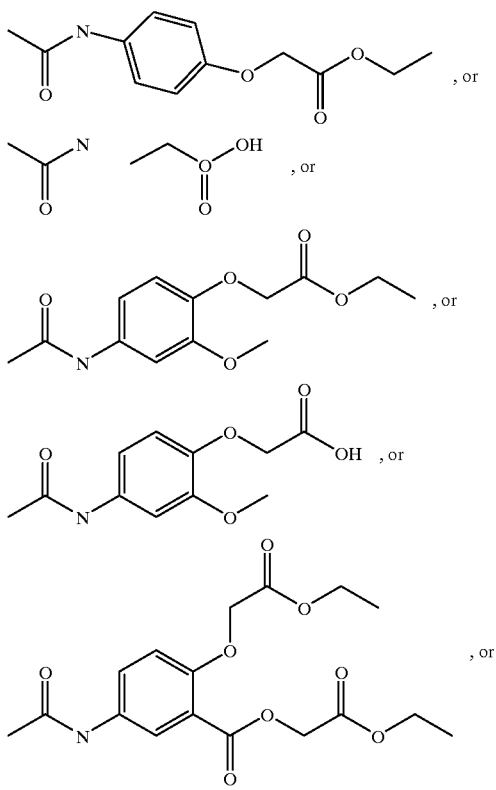

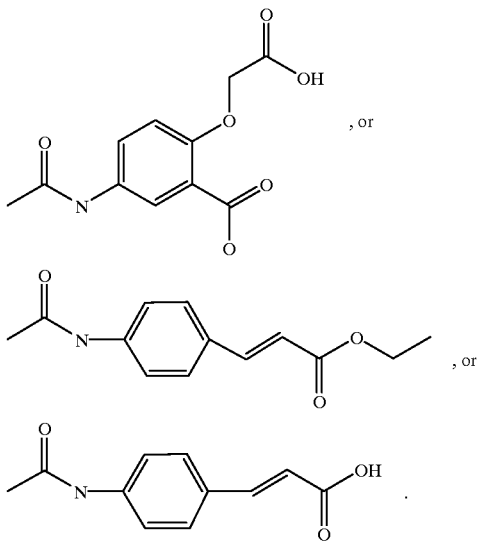

33. The compound in accordance with claim 32, which is ethyl (4-{[2-(3-benzyl-ureido)-thiazole-4-carbonyl]-amino}-phenoxy)-acetate.

34. The compound in accordance with claim 32, which is [4-[[2-(3-benzyl-ureido)-thiazole-4-carbonyl]-amino-phenoxy]-acetic acid.

35. The compound in accordance with claim 32, which is ethyl (4-{[2-(3-benzyl-ureido)-thiazole-4-carbonyl]-amino}-2-methoxy-phenoxy)-acetate.

36. The compound in accordance with claim 32, which is (4-{[2-(3-benzyl-ureido)-thiazole-4-carbonyl]-amino}-2-methoxy-phenoxy)-acetic acid.

37. The compound in accordance with claim 32, which is ethoxycarbonylmethyl 5-{[2-(3-benzyl-ureido)-thiazole-4-carbonyl]-amino}-2-ethoxycarbonylmethoxy-benzoate.

38. The compound in accordance with claim 32, which is 5-{[2-(3-benzyl-ureido)-thiazole-4-carbonyl]-amino}-2-carboxymethoxy-benzoic acid.

39. The compound in accordance with claim 32, which is ethyl (E)-3-[4-[[2-(3-benzyl-ureido)-thiazole-4-carbonyl]-amino]-phenyl]-acrylate.

40. The compound in accordance with claim 32, which is (E)-3-[4-[2-(3-benzyl-ureido)-thiazole-4-carbonyl]-amino]-phenyl]-acrylic acid.

41. The compound in accordance with claim 1, which is methyl [4-{[2-(3-benzyl-ureido)-thiazole-4-carbonyl]-amino}-phenyl)-phenyl-amino]-acetate in the form of an amorphous powder.

42. The compound in accordance with claim 1, which is butyl {3-[(2-guanidino-4-methyl-thiazole-5-carbonyl)-amino-propoxy}-acetate.

43. The compound in accordance with claim 1, which is methyl [(4-{[2-(3-benzyl-ureido)-thiazole-4-carbonyl]-amino}-phenyl)-phenylamino]-acetate.

44. The compound in accordance with claim 1, wherein $R^1$ is

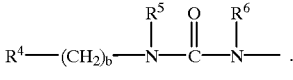

45. The compound in accordance with claim 1, wherein $R^1$ is

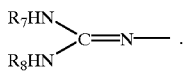

46. The compound in accordance with claim 1, wherein $R^1$ is

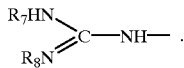

47. The compound in accordance with claim 1, wherein $R^3$ is hydrogen, alkyl, cycloalkyl, carboxy, or alkyl-O—CO.

48. The compound in accordance with claim 1, wherein $R^3$ is aryl, aralkyl, heteroaryl, or aralkyl-O—CO.

49. The compound in accordance with claim 1, wherein $R^4$ is hydrogen, alkyl or cycloalkyl.

50. The compound in accordance with claim 1, wherein $R^4$ is aryl or heteroaryl.

51. The compound in accordance with claim 1, wherein $R^5$ and $R^6$, independent of one another, are hydrogen, alkyl, or cycloalkyl.

52. The compound in accordance with claim 1, wherein wherein $R^5$ and $R^6$ are heteroaryl.

53. The compound in accordance with claim 1, wherein $R^7$ and $R^8$, independent of one another, are hydrogen, alkyl, or cycloalkyl.

54. The compound in accordance with claim 1, wherein $R^7$ and $R^8$ are heteroaryl.

55. The compound in accordance with claim 1, wherein $R^7$ and R9 together with the N atoms to which they are attached form a 5- to 8-membered heterocyclic ring or a 5- to 8-membered heterocyclic ring that is substituted with one or more alkyl substituents.

56. The compound according to claim 1, wherein $R^{10}$ is hydrogen, heterocyclylalkyl, carboxyalkyl, alkyl cycloalkyl, alkyl-O—CO—, alkyl-CO—, or alkyl sulphonyl.

57. The compound according to claim 1, wherein $R^{10}$ is aryl, aralkyl, heteroaryl, aralkyl-O—CO—, arylsulphony, or heteroaryl sulphonyl.

* * * * *

UNITED STATES PATENT AND TRADEMARK OFFICE
CERTIFICATE OF CORRECTION

PATENT NO. : 6,297,266 B1 Page 1 of 1
DATED : October 2, 2001
INVENTOR(S) : Alig et al.

It is certified that error appears in the above-identified patent and that said Letters Patent is hereby corrected as shown below:

Column 31,
Line 42, delete "allcyl" and replace with -- alkyl --; and

Column 40,
Line 11, delete "R9" and replace with -- $R^8$ --.

Signed and Sealed this

Fourteenth Day of May, 2002

Attest:

JAMES E. ROGAN
Attesting Officer   Director of the United States Patent and Trademark Office